United States Patent [19]

Koszyk et al.

[11] Patent Number: 5,219,883
[45] Date of Patent: Jun. 15, 1993

[54] 2,2-DI-SUBSTITUTED BENZOPYRAN LEUKOTRIENE-$D_4$ ANTAGONISTS

[75] Inventors: Francis J. Koszyk, Chicago; James R. Deason, Wilmette, both of Ill.

[73] Assignee: G. D. Searle & Co., Chicago, Ill.

[21] Appl. No.: 790,976

[22] Filed: Nov. 12, 1991

Related U.S. Application Data

[62] Division of Ser. No. 532,768, Jun. 4, 1990, Pat. No. 5,093,353, which is a division of Ser. No. 196,996, May 20, 1988, Pat. No. 4,950,684.

[51] Int. Cl.$^5$ .................. C07D 311/22; A61K 31/35
[52] U.S. Cl. ...................................... 514/456; 549/401
[58] Field of Search ............... 549/399, 401, 402, 403; 514/460, 456

[56] References Cited

U.S. PATENT DOCUMENTS

| | | | |
|---|---|---|---|
| 3,882,148 | 5/1975 | Augstein et al. | 549/402 |
| 3,952,013 | 4/1976 | Hazard et al. | 549/23 |
| 3,953,604 | 4/1976 | Warren et al. | 548/253 |
| 4,006,245 | 2/1977 | Augstein et al. | 514/456 |
| 4,133,889 | 1/1979 | Augstein et al. | 514/382 |
| 4,156,726 | 5/1979 | Brown et al. | 546/108 |
| 4,213,903 | 7/1980 | Bantick et al. | 548/250 |
| 4,234,726 | 11/1980 | Gardner | 544/151 |
| 4,238,495 | 12/1980 | Warren et al. | 514/382 |
| 4,281,008 | 7/1981 | Chamberlain et al. | 514/385 |
| 4,328,230 | 5/1982 | Brown et al. | 546/88 |
| 4,546,194 | 10/1985 | Miyano et al. | 549/401 |
| 4,565,882 | 1/1984 | Miyano et al. | 549/402 |
| 4,665,203 | 5/1987 | Miyano et al. | 549/402 |
| 4,889,871 | 12/1989 | Djuric | 549/401 |

FOREIGN PATENT DOCUMENTS

| | | |
|---|---|---|
| 0079637 | of 0000 | European Pat. Off. |
| 0129906 | 6/1983 | European Pat. Off. |
| 0139809 | 5/1985 | European Pat. Off. |
| 2089338 | 6/1982 | United Kingdom |

OTHER PUBLICATIONS

Chemical Abstracts, CA 97:16807g (1982).
Appleton, et al., "Antagonists of Slow Reacting Substance of Anaphylaxis...", J. Med. Chem., 20, 371-379 (1977).
Augstein, et al., "Selective Inhibitor of Slow Reacting Substance of Anaphylaxis", Nature New Biology, 245, 215-217 (1973).

*Primary Examiner*—C. Warren Ivy
*Assistant Examiner*—Celia Chang
*Attorney, Agent, or Firm*—Mary Jo Kanady; Paul D. Matukaitis

[57] ABSTRACT

This invention relates to $LTD_4$ antagonists of the formula:

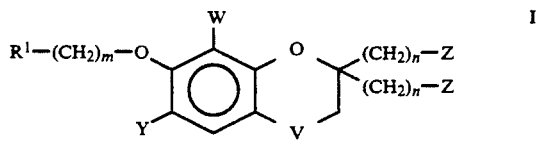

or pharmaceutically acceptable salts thereof, wherein $R^1$ is methyl, phenyl,

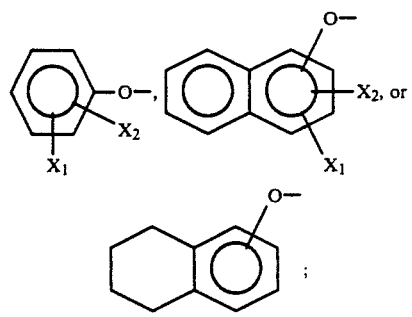

wherein $X_1$ and $X_2$ may be the same or different and are members of the group consisting of hydrogen, —Cl, —Br, —$CF_3$, —$NH_2$, —$NO_2$, or alkyl of 1–3 carbon atoms; m is 1 to 9; n is 1 to 5; V is —CH(OH)—, or —$CH_2$—; W is hydrogen or alkyl of 1–6 carbon atoms; Y is hydrogen or —$COCH_3$ provided that when W is hydrogen Y is not hydrogen; both Z moieties are —CHO, —$COOR^2$, —$COR^3$, —CH($OR^4$)—$CH_2OR^4$, (Abstract continued on next page.)

or $CH_2OR^4$ with the exception that when one Z moiety of Formula I is $COOR^2$, the other Z moiety may be $COR^3$;

$R^2$ is hydrogen, a pharmaceutically acceptable cation, straight or branched chain alkyl having 1-6 carbon atoms, $-CH_2-CH(OR^5)-CH_2-OR^5$, $CH(CH_2OR^5)_2$ with the proviso that when Z is $-COOR^2$, the $R^2$ substituent in one $-COOR^2$ moiety may be the same or different from the $R^2$ substituent in the other $COOR^2$ moiety;

$R^3$ is $-NR^7R^8$ wherein $R^7$ and $R^8$ may be the same or different and are members of the group comprising hydrogen or alkyl having 1-6 carbon atoms;

$R^4$ is hydrogen, or $-C(O)-R^6$;

$R^5$ is hydrogen, benzyl-, or alkyl or 1-3 carbon atoms; and $R^6$ is alkyl of 1-6 carbon atoms.

18 Claims, No Drawings

2,2-DI-SUBSTITUTED BENZOPYRAN LEUKOTRIENE-D₄ ANTAGONISTS

This is a divisional of pending application Ser. No. 07/532,768, filed Jun. 4, 1990, now U.S. Pat. No. 5,093,353, issued Mar. 3, 1988, which is a division of application Ser. No. 07/196,996 filed May 20, 1988 and issued as U.S. Pat. No. 4,950,684 on Aug. 21, 1990.

BACKGROUND OF THE INVENTION

1. Field of the Invention

This invention relates to novel compounds of Formula I having a 2,2-di-substituted chromanonyl (benzopyran) ring-structure which are antagonists of leukotriene D₄ (LTD₄) and the slow reacting substance of anphylaxis (SRS-A). In particular, the compounds of this invention are useful as pharmaceutical agents to prevent or alleviate the symptoms associated with LTD₄, such as allergic reactions and inflammatory conditions.

LTD₄ is a product of the 5-lipoxygenase pathway and is the major active constituent of slow reacting substance of anaphylaxis (SRS-A), a potent bronchonconstrictor that is released during allergic reactions. See R. A. Lewis and K. F. Austen, *Nature*, 293, 103-108 (1961). When administered to humans and guinea pigs, LTD₄ causes bronchoconstriction by two mechanisms: (1) directly, by stimulating smooth muscle; and (2) indirectly, through release of thromboxin A₂ which then causes contraction of respiratory smooth muscle. Because antihistamines are ineffective in the management of asthma, SRS-A and not histamine is believed to be a mediator of the bronchoconstriction occurring during an allergic attack. LTD₄ may also be involved in other inflammatory conditions such as rheumatoid arthritis. Furthermore, LTD₄ is a potent coronary vasoconstrictor and influences contractile force in the myocardium and coronary flow rate of the isolated heart. See F. Michelassi, et al., *Science*, 217, 841 (1982); J. A. Burke, et al., *J. Pharmacol, and Exp. Therap.*, 221, 235 (1982).

2. Prior Art

Appleton, et al., *J. Med. Chem.*, 20, 371-379 (1977) discloses a series of chromone-2-carboxylic acids having a single substituent in the 2-position, which are antagonists of SRS-A. Specifically, sodium 7-[3-(4-acetyl-3-hydroxy-2-propylphenoxy)-2-hydroxypropoxy]-4-oxo-8-propyl-4H-1-benzopyran-2-carboxylate (FPL 55712), appears to be the first reported specific antagonist of SRS-A and LTD₄.

Miyano, et al., (U.S. Pat. No. 4,546,194) discloses substituted chromanon-2-yl alkanols and derivatives thereof which are useful as LTD₄ inhibitors. In Miyano, the LTD₄ inhibitors have two substituents at the two position of their chromane ring, one of which is alkyl. Moreover, Miyano discloses a diether at position 7 which has 4-acetyl-3-hydroxy-2-propylphenoxy as the substituent at its terminus.

Similar references disclosing chromane compounds which are useful as LTD₄ antagonists are the following: European Patent Application Nos. 0079637, 129,906, and 150,447; U.S. Pat. No. 4,565,882; Japanese patent 60/42378; and C. A. 103(19) 160 389 G.

SUMMARY OF THE INVENTION

This invention encompasses a compound of the formula:

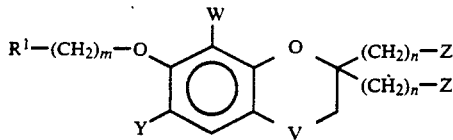

or a pharmaceutically acceptable addition salt thereof, wherein $R^1$ is methyl, phenyl,

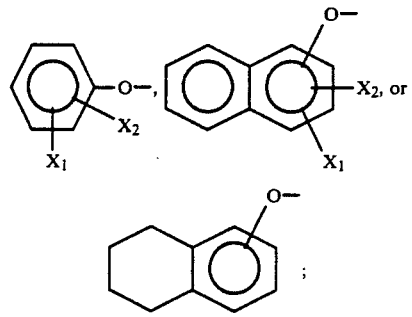

wherein $X_1$ and $X_2$ may be the same or different and are hydrogen, —Cl, —Br, —CF₃, —NH₂, —NO₂, or straight or branched chain alkyl of 1-3 carbon atoms;
wherein m is an integer from 1-9;
wherein n is an integer from 1-5;
wherein V is

—CH(OH)—, or —CH₂—;
wherein W is hydrogen or straight or branched chain alkyl of 1-6 carbon atoms;
wherein Y is hydrogen or —COCH₃;
wherein Z is —CHO, —COOR², —COR³,

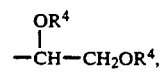

or CH₂OR⁴ with the proviso that when one moiety of Formula I is COOR², the other Z moiety may optionally be COR³;
wherein $R^2$ is hydrogen, a pharmaceutically acceptable cation, straight or branched chain alkyl having 1-6 carbon atoms,

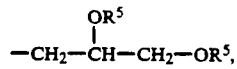

or —CH(CH₂OR⁵)₂
with the proviso that when Z is —COOR², the $R^2$ substituent in one —COOR² moiety may be the same or different from the $R^2$ substituent in the other COOR² moiety;
wherein $R^3$ is

and wherein $R^7$ and $R^8$ may be the same or different and are members of the group comprising hydrogen or straight or branched chain lower alkyl having 1–6 carbon atoms; or wherein N, $R^7$ and $R^8$ may together form a cyclic amine of the formula

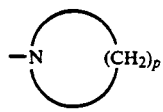

wherein p is 4 or 5;
wherein $R^4$ is hydrogen, or

wherein $R^5$ is hydrogen, benzyl-, or straight or branched chain alkyl of 1–3 carbon atoms; and
wherein $R^6$ is a member of the group comprising straight or branched chain alkyl having 1–6 carbon atoms.

DETAILED DESCRIPTION

This invention relates to novel $LTD_4$ inhibitors of Formula I having a chromane ring structure and 2,2-disubstitution on the chromane ring. The disubstituents of the present invention are of the formula $-(CH_2)_m-Z$ wherein Z is a carbonyl containing moiety such as $-CHO$, $-COOR^2$, or $-COR^3$, i.e. an aldehyde, ester, or amide respectively; or an alcohol, i.e. the reduction product of the above carbonyls; or the corresponding lower alkyl ester of said alcohol.

The term "lower alkyl" as used herein means straight or branched chain alkyl having 1–6 carbon atoms such as methyl, ethyl, propyl, butyl, pentyl, hexyl and the isomeric forms thereof.

The term "pharmaceutically acceptable cation" as used to describe $R^2$ refers to cations such as ammonium, sodium, potassium, lithium calcium, magnesium, ferrous, zinc, copper, manganous, aluminum, ferric, manganic, ammonium, tetraalkylammonium, and the like.

The term "pharmaceutically acceptable addition salts" refers either to those base derived salts of any compound herein having a carboxylic acid function, or to those acid derived salts of any compound herein having an amide function.

The base derived salts may be derived from pharmaceutically acceptable non-toxic inorganic or organic bases. Among the inorganic bases employed to produce said pharmaceutically acceptable salts are the hydroxide bases of the pharmaceutically acceptable cations disclosed above.

Among the organic bases employed to produce said pharmaceutically acceptable salts are the pharmaceutically acceptable non-toxic bases of primary, secondary, and tertiary amines. Especially preferred non-toxic bases are isopropylamine, diethylamine, ethanolamine, dicyclohexylamine, choline, and caffein.

The acid derived salts may be derived from pharmaceutically acceptable non-toxic organic or inorganic acids. Suitable pharmaceutically acceptable organic acid salts include such salts as the maleate, fumarate, tartrate, (methane-, ethane-, and benzene) sulfonates, citrate, and the malate. Suitable inorganic (mineral) acid salts include such salts as the chloride, bromide, and sulfate.

All the pharmaceutically acceptable non-toxic addition salts are prepared by conventional processes well known to those of ordinary skill in the art.

$LTD_4$ acts by causing brochoconstriction in both guinea pigs and humans. The bronchoconstriction has two components: (1) a direct component, wherein $LTD_4$ stimulates the respiratory smooth muscle to constrict; and (2) an indirect component wherein $LTD_4$ causes the release of thromboxane A2 which also causes the construction of respiratory smooth muscle. The compounds of this invention act by antagonizing the direct constriction of respiratory smooth muscle by $LTD_4$.

The $LTD_4$ antagonistic activity of the compounds of this invention were determined by both in vivo and in vitro testing upon guinea pigs. In one in vivo assay, adult male fasted Hartly guinea pigs weighing 300–360 g were pretreated with pyrilamine and indomethacin to block the bronchoconstrictive effects of endogenous histamine and the synthesis of thromboxane A2 respectively. Compounds of the invention were administered IG (intragastrically) at approximate times prior to the IV (intravenous) administration of 2000 units of $LTD_4$. Intratracheal pressure was monitored prior to and subsequent to $LTD_4$ administration in animals anesthetized with pentobarbital and attached to a rodent respirator. A compound was determined to antagonize the direct component of $LTD_4$ action on respiratory smooth muscle if the compound inhibited the intratracheal insufflation pressure increases caused by $LTD_4$. The compounds of this invention were found to exhibit $LTD_4$ antagonistic activity at doses of 10 mg/kg.

One of the in vitro assays utilized to determine the $LTD_4$ antagonistic activity of the compounds of this invention was performed on excised guinea pig ileum (smooth muscle). In this assay, control contractions of guinea pig ileum ("ileum") were incubated in a solution of $LTD_4$ and the number of contractions in response to $LTD_4$ were determined. A solution or suspension containing a compound of this invention was substituted for the control solution and the item was allowed to incubate for 30 minutes. Thereafter, doses of $LTD_4$ were added and increased if necessary until contractions were obtained that are approximately equal to the control. A dose/test compound ratio was calculated from the results of each test. A concentration of the test compound was judged to be active if it produced a dose ratio that was significantly greater than that obtained in a series of blank treatment tests. Duplicate tests were conducted on each concentration of test compound. Initial screening of the compounds of this invention began at $3 \times 10^{-6}M$. The compounds of the present invention were determined to exhibit $LTD_4$ antagonistic activity at test concentration ranging from $3 \times 10^{-6}M$ to $1 \times 10^{-7}M$.

By virtue of their activity as $LTD_4$ inhibitors, the compounds of Formula I are useful in treating inflammatory conditions in mammals in which $LTD_4$ plays a role such as psoriasis, Chrohn's disease, asthmatic bronchitis, ulcerative colitis and the like. A physician or veterinarian or ordinary skill can readily determine whether a subject exhibits the inflammatory condition. The preferred utility relates to treatment of ulcerative colitis.

The compounds can be administered in such oral dosage forms as tablets, capsules, softgels, pills, powders, granules, elixirs, or syrups. The compounds may also be administered intravascularly, intraperitoneally, subcutaneously, intramuscularly, or topically using forms known to the pharmaceutical art. In general, the preferred form of administration is oral or in such a manner so as to localize the inhibitor. For example, for asthma, the compounds could be inhaled using an aerosol or other appropriate spray. In an inflammatory condition such as rheumatoid arthritis, the compounds could be injected directly into the affected joint.

For the orally administered pharmaceutical compositions and methods of the present invention the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, the active drug components may be combined with ay oral non-toxic pharmaceutically acceptable inert carrier such as lactose, starch, sucrose, cellulose, magnesium stearate, dicalcium phosphate, calcium sulfate mannitol, and the like, or various combination thereof. For oral administration in liquid forms, such as in softgels, elixirs, syrups, drops and the like, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, intramuscular or aerosol administration, active drug components may be combined with a suitable carrier such as water, saline, aqueous dextrose, and the like. Regardless of the route of administration selected, the compounds of the present invention are formulated into pharmaceutically acceptable dosage forms by conventional methods known to those skilled in the art. The compounds may also be formulated using pharmacologically acceptable acid or base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained.

The compounds of this invention are prepared by the general methods illustrated in Schemes A–E. In the discussion of these schemes, the conventional numbering of the chromane ring is employed as illustrated in Formula II below.

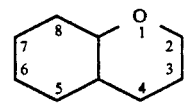

II

In charts A to E, the various compounds and intermediates can be readily modified by methods known to those skilled in the art. For example, esters can be hydrolyzed to corresponding carboxylic acids (and their respective addition salts), or converted to corresponding amides by appropriate reactions with amines, or reduced to alcohols by such reagents as lithium aluminium hydride ($LiAlH_4$). Such products and intermediates can, or course, be similarly interconverted.

As illustrated in Chart A, 2,4-dihydroxylacetophenones of Formula X, wherein W and Y are as defined herein, react readily with ketodiesters of Formula XI, such as dimethyl 4-oxopimelate where (n=2), to afford fused ring compounds of Formula XII or of Formulas XII and XIII depending upon reaction conditions. The preferred reaction conditions for condensation and cyclization to produce the compound of Formula XII include heating Formulas X and XI in toluene, in the presence of a base such as pyrrolidine, with provisions for removal of the water with an apparatus such as a Dean-Stark trap. Alternatively, to produce the compounds of both Formulas XII and XIII, the condensation and cyclization is allowed to proceed overnight at room temperature in the presence of a secondary amine, such as pyrrolidine, and then at reflux for about 3–4 hours.

The intermediates of Formulas XII and XIII may be used in reactions in Chart B without further modification or they may be converted to related intermediates of Formulas XIV and XV by methods known to those skilled in the art. For example, hydrogenation over palladium on carbon (Pd/C) will reduce the keto function of the dihydrobenzopyran-4-ones (Formulas XII or XIII) to the corresponding —$CH_2$—, producing a dihydrobenzopyran of Formula XIV. Partial hydrogenation or reduction with $NaBH_4$ in a polar solvent will afford the corresponding 4-hydroxy compound of Formula XV. These latter two sequences of reactions provide the means for achieving the necessary diversity in "V" of Formula I.

As illustrated in Chart B, alcohols of the formula $R^1OH$ (XVIa) may be alkalyated to form ethers in the presence of an alkylating agent (XVIb) and a base. Preferably, the alcohol is methanol or hydroxyaryl. By "hydroxyaryl" is meant phenol, naphthol, 5,6,7,8-tetrahydronaphthols or substituted analogs thereof, wherein the substituents include —$NH_2$, $NO_2$, Cl, Br, $CF_3$ and lower alkyl from 1–4 carbon atoms. Preferably, the alkylating agent is a dihaloalkane of the formula X—$(CH_2)_m$—X wherein X is Br, Cl or I and m is an integer from 1–9. Especially preferred as an alkylating agent is Br—$(CH_2)_m$—Br. Preferred reaction conditions include reaction in dry dimethylformamide (DMF) in the presence of the anhydrous base, potassium carbonate.

Intermediates of Formula XVII are typically purified by column chromatography on silica gel. The further reaction of XVII with 7-hydroxybenzopyran-4-ones of Formula XII in the presence of base in polar aprotic solvents afford the diester pyranone ethers (XVIII) of this invention. Similarly, diester pyran and pyranol ethers can be afforded by reaction of XVII with pyrans of Formula XIV and pyranols of Formulas XV, respectively. Preferred reaction conditions for this ether formation include reaction in dry DMF in the presence of an anhydrous base, such as potassium carbonate.

Chart B further illustrates that the diesters XVIII may be hydrolyzed to the corresponding diacid salt XIX in the presence of a base. Preferably, the base is a hydroxide species having a pharmaceutically acceptable cation as disclosed herein. The preferred solvent system is aqueous alcohol, such as aqueous methanol. The resulting diacid salts XIX may be converted to the corresponding diacid species XX by acidification of XIX in an aqueous alcoholic solution. Preferred acidifying agents are the mineral acids such as HCl, $H_2SO_4$, $H_3PO_4$ and the like.

Chart C illustrates the preparation of the compounds of Formula XVIII using a variation of the method of Chart B. The compounds of Formula XII are first reacted with dihaloalkanes of the formula, X—$(CH_2)_m$—X, preferably Br—$(CH_2)_m$—Br, in the presence of base in a polar solvent to produce an intermediate of Formula XXI. As in Chart B, the preferred conditions for ether formation include reaction in dry dimethyl formamide (DMF) in the presence of anhydrous potassium carbonate ($K_2CO_3$). By the same general procedure for ether formation just employed in converting Formula XII to XXI above, Formulas XXI and X react in the presence of base in a polar solvent to form the title compounds of this invention, Formula XVIII.

Chart D illustrates a condensation reaction analogous to Chart A wherein 2,4-dihydroxyacetophenones of Formula X react with ketodienes of Formula XXX in the presence of a weak base in a nonpolar solvent with heat to afford the corresponding 2,2-bis-enylpyranone's of Formula XXXI. Preferred reaction conditions include toluene as the solvent and pyrrolidine as the weak base. Formula XXXI reacts with a halide XVII in a polar solvent, preferably dimethylformamide (DMF), in the presence of a base, preferably $K_2CO_3$, via a nucleophilic substitution to form the corresponding bis-(enyl)ether XXXII. The enyl groups of XXXII are oxidized to the vicinal diols of XXXIII by $OsO_4$ in aqueous alcoholic tetrahydrofuran (THF) in the presence of N-methylmorpholine-N-oxide. Preferably, the alcoholic portion of the solvent is t-butanol.

Chart E illustrates further reactions of the bis-diol XXXIII to yield the compounds of this invention. The bis-diol XXXIII may be esterified to a tetraester XXXIV by acetylation - reaction of the bis-diol with an excess of an alkyl or aryl anhydride such as acetic anhydride in the presence of a weak base, preferably pyridine. Alternatively, the bis-diol XXXIII can be oxidized to a bis-aldehyde, wherein the oxidized side chain loses one carbon atom. The preferred oxidizing agent is periodate ($IO_4$—) associated with either H+ or an alkali metal cation.

In another reaction sequence in Chart E, the diester XVII is first converted to the diacyl chloride by reaction with thionyl chloride ($SO_2Cl$) and then to the bis-(dibenzyl ester) XXXVI by reaction of the diacyl chloride with 1,3-dibenzyloxy-2-propanol. Partial hydrogenation of XXXVI over 10% Pd/C produces the tetra-ol XXXVII. Alternatively, the diester XVIII may be converted to the terminal bis-(diol ester) XXXVIII by reaction with glicidol in the presence of benzyl-trimethylammonium hydroxide.

It is recognized that certain compounds of this invention may exist in L, D and D, L forms. These stereoisomers may be separated into their individual enantiomers by techniques well known in the art, such as recrystallization and chromatography of their optically active derivatives.

The following examples are given by way of illustration only and should not be construed as limiting this invention either in spirit or in scope, as based upon the disclosure herein many variations will become obvious to those of ordinary skill in the art.

CHART A

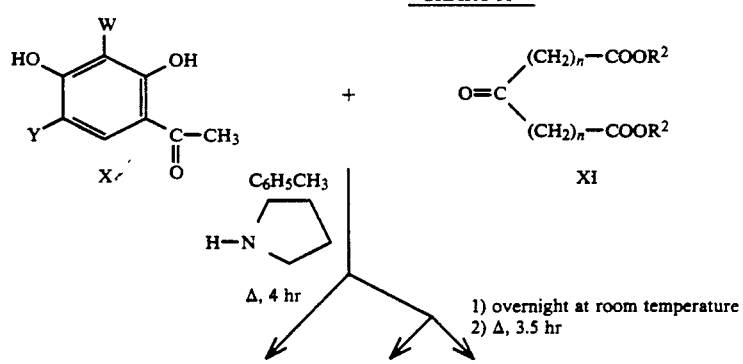

CHART A
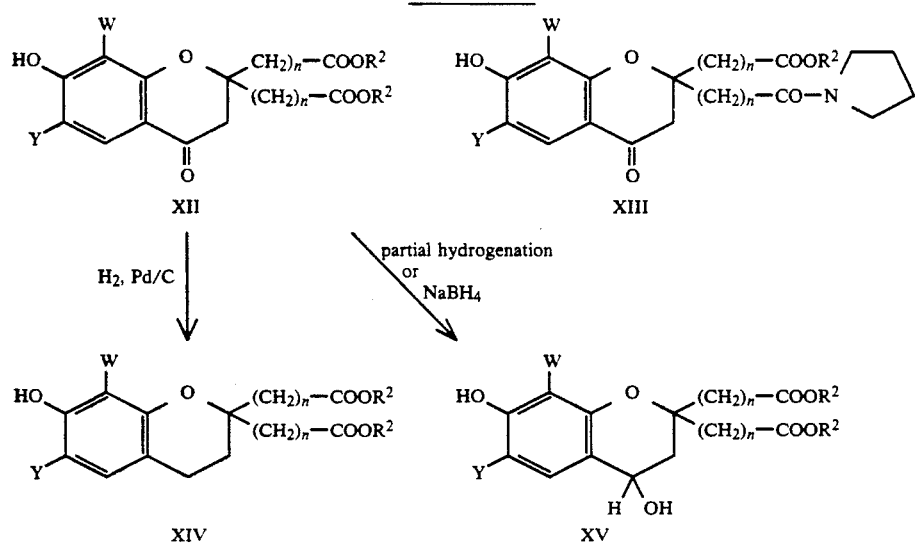
CHART B
When $R^1$ = Aryl—O—, start here: $R^1H$ + H—$(CH_2)_m$—X
XVIa    XVIb
↓ base
When $R^1$ = $CH_3$ or phenyl, start here: $R^1$—$(CH_2)_m$—X
XVII
XII —→ $K_2CO_3$ / DMF
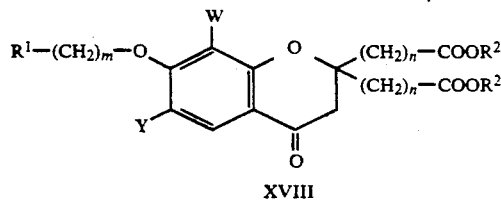
XVIII
NaOH, $CH_3OH$, $H_2O$
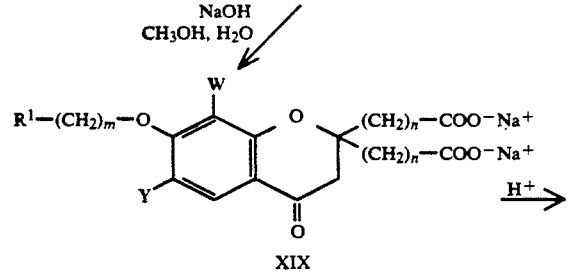
XIX
$\overset{H^+}{\longrightarrow}$
$\begin{cases} \text{—COOH} \\ \text{—COOH} \end{cases}$
XX
CHART C
XII + Br—$(CH_2)_m$—Br
↓ $K_2CO_3$, DMF
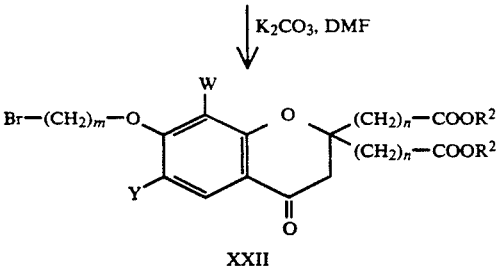
XXII
↓ $R^1H$, $K_2CO_3$, DMF, Δ
(when $R^1$ = Aryl—O—)
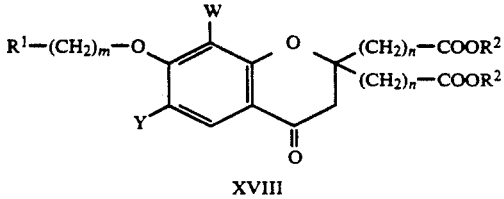
XVIII

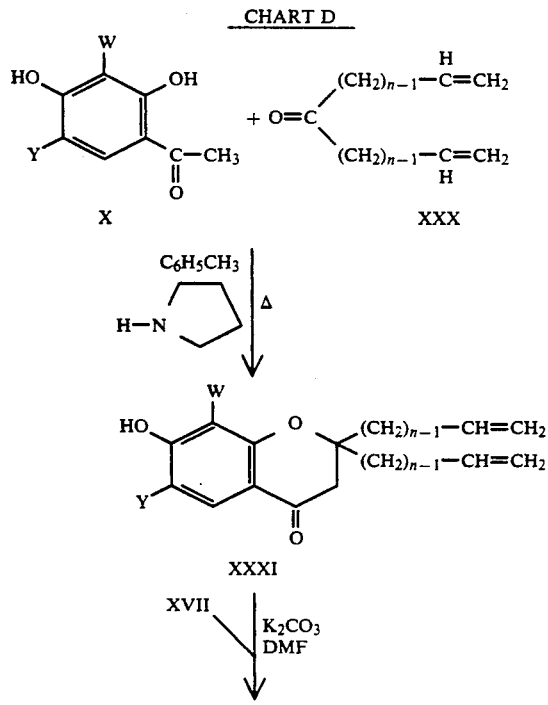

CHART E

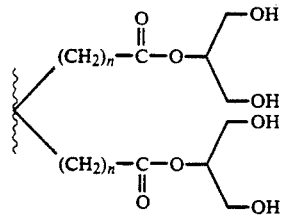

XXXVII

DESCRIPTION OF THE PREFERRED EMBODIMENT

EXAMPLE 1 diethyl 3,4-dihydro-4-oxo-7-hydroxy-8-propyl-2H-1-benzopyran-2,2-dipropanoate

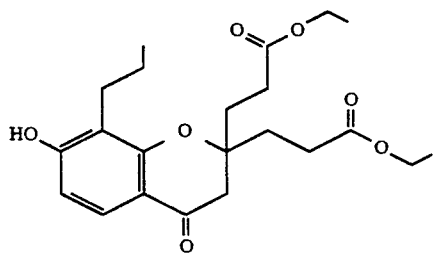

A stirred solution of 12.3 g (53.5 mmol) of diethyl 4-oxopimelate, 10.4 g (53.5 mmol) of 2,4-dihydroxy-3-propylacetophenone, and 3.8 g (55 mmol) of pyrrolidine in 62 ml of toluene was refluxed under a water separator. After 4 hours, the mixture was allowed to cool. The solvent was removed under reduced pressure and the resultant oil was chromatographed on silica gel using ethyl acetate-hexane as eluent. The titled diester (4.98 g) was found to be homogeneous by thin-layer chromatography (20% by volume ethyl acetate/hexane on silica gel plates) and was used in subsequent reactions without further purification.

$^1$H NMR (CDCl$_3$): δ8.13(br s, 1H); 7.60(d, J=9 Hz, 1H); 6.50 (d, J=9 Hz, 1H); 4.12(q, J=7 Hz, 4H); 2.65(br s, 2H); 2.53-1.83(m, 10H); 1.52 (m, 2H); 1.22(q, J=7 Hz, 6H); and 0.95(t, 3H).

EXAMPLE 2

Mixture of dimethyl 3,4-dihydro-4-oxo-7-hydroxy-8-propyl-2H-1-benzopyran-2,2-dipropanoate and

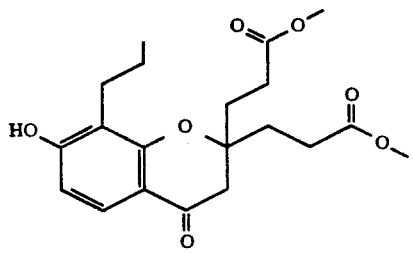

methyl 3,4-dihydro-4-oxo-2-(3-oxo-3-[1-pyrrolidinyl]propyl)-8-propyl-7-hydroxy-2H-1-benzopyran-2-propanoate

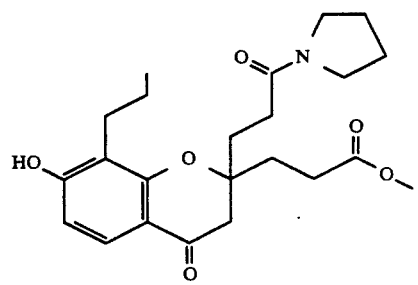

A stirred solution of 9.70 g (50 mmol) of 2,4-dihydroxy-3-propylacetophenone, 10.1 g (50 mmol) of dimethyl 4-oxopimelate, and 1.8 g of pyrrolidine in 62 ml of toluene was stirred overnight at room temperature, then refluxed under a water separator for 3.5 hours. The mixture was allowed to cool, and the solvent was removed under reduced pressure. Chromatography of the residue on silica gel using 20% ethyl acetate/toluene as eluent gave 1.39 g of the titled diester. The purified diester was found to be homogeneous by thin-layer chromatography (20% ethyl acetate/toluene by volume on silica gel plates) an was used in subsequent reactions without further purification. The titled ester-amide (590 mg) was obtained impure but was suitable for use in subsequent reactions.

Diester: $^1$H NMR (CDCl$_3$): δ0.99(t, 3H); 1.21-1.75(m, 2H); 1.91-2.75(m, 10H); 2.66(s, 2H); 3.68(s, 6H); 5.91(br s, 1H); 6.45(d, 1H) and 7.63(d, 1H).

Ester-amide: $^1$H NMR (CDCl$_3$): δ10.45(br s, 1H); 7.56(d, 1H); 6.64(d, 1H); 3.68(s, 3H); 2.82(br s, 2H); 1.57(m, 2H); and 1.01(t, 3H).

EXAMPLE 3

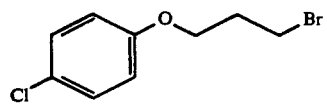

To a suspension of 1.53 g (63.8 mmol) of sodium hydride in 50 ml of dry dimethylformamide was added over thirty minutes a solution of 8.23 g (63.8 mmol) of 4-chlorophenol. After stirring for one hour at room temperature, 16 g (77 mmol) of 1,3-dibromopropane was added in one portion. The mixture was stirred for 68 hours, and the solvent removed under reduced pressure. The residue was dissolved in diethyl ether and washed with water. The aqueous layer was then extracted twice with ether. The combined organic extracts were washed three times with water, once with brine, then dried (MgSO₄). After filtration, the solvent was removed under reduced pressure. The residue was chromatographed on silica gel, using 10% methylene chloride/hexane as the eluent and produced 710 mg of the title compound, which was homogenous by thin layer chromatography (10% by volume of methylene chloride/hexane on silica gel plates).

¹H NMR (CDCl₃): δ7.27(d, J=9 Hz, 2H); 6.85(t, J=9 Hz, 2H); 4.07 (t, 2H), 3.60(t, 2H); and 2.28(quintet, 2H).

EXAMPLE 4

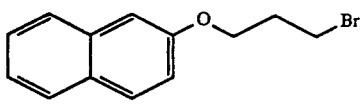

To a solution of 3.60 g (25 mmol) of 2-naphthol and 6.0 g (30 mmol) of 1,3-dibromopropane in dimethylformamide was added 7.25 g (52.5 mmol) of finely ground anhydrous potassium carbonate. The mixture was stirred vigorously overnight. Solvent was removed under reduced pressure. The residue was partitioned between ethyl acetate and water. The aqueous layer was further extracted twice with ethyl acetate. The combined organic extracts were dried over magnesium sulfate, and after filtration, the solvent was removed under reduced pressure. The residue was then chromatographed over silica gel using 10% methylene chloride/hexane as eluent to afford 1.66 g of the title compound, which was homogeneous by thin layer chromatography (5% by volume of ethyl acetate/hexane on silica gel plates).

¹H NMR (CDCl₃): δ7.73–6.90(m, 7H); 4.03(t, 2H); 3.50(t, 2H); and 2.22(quintet, 2H).

EXAMPLE 5

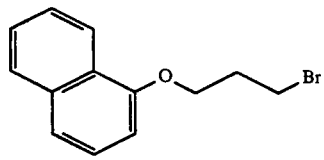

The title compound was prepared by the method of Example 4 using 1-naphthol, 1.80 g (12.5 mmol), in place of 2-naphthol. After chromatography there was obtained 0.80 g of the title compound, which was homogeneous by thin layer chromatography (10% by volume of toluene/hexane on silica gel plates).

¹H NMR (CDCl₃): δ8.40–6.77(m, 7H); 4.22(t, 2H); 3.65(t, 2H); and 2.38(quintet, 2H).

EXAMPLE 6

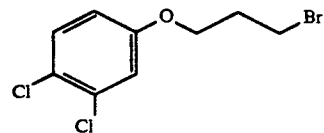

A mixture of 3.26 g (20 mmol) of 3,4-dichlorophenol, 20.2 g (100 mmol) of 1,3-dibromopropane, 6.80 g (20 mmol) of tetra-n-butyl ammonium hydrogen sulfate, 40 ml of 1N sodium hydroxide, and 40 ml of methylene chloride was stirred rapidly at reflux. After 2 hours, the mixture was allowed to cool and the layers were separated. The organic layer was washed with water, dried over magnesium sulfate, filtered and the solvent removed under reduced pressure. The residue was chromatographed over silica gel using methylene chloride/hexane as eluent. The title compound (1.58 g) was found to be homogeneous by thin layer chromatography (10% by volume of methylene chloride/hexane on silica gel plates).

¹H NMR (CDCl₃): δ7.29(d, J=9 Hz, 1H); 6.97(d, J=3 Hz, 1H); 6.71 (dd, J=3, J=9 Hz, 1H); 3.97(t, 3H); 3.57(t, 2H); 2.27(quintet, 2H).

EXAMPLE 7

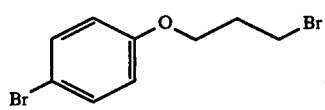

The title compound was prepared and worked up by the method of Example 6 using 4-bromophenol in place of 3,4-dichlorophenol. After chromatography the title compound (3.45 g) was found to be homogeneous by thin layer chromatography (10% by volume of methylene chloride/hexane on silica gel plates).

¹H NMR (CDCl₃): δ7.31(d, 2H); 6.71(d, 2H); 3.98(t, 2H); 3.50(t, 2H); and 2.20(quintet, 2H).

EXAMPLE 8

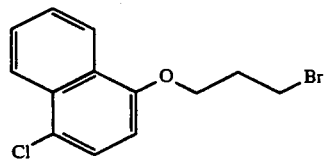

The title compound was prepared and worked up according to the method of Example 6 using 4-chloro-1-naphthol (1.79 g) in place of 3,4-dichlorophenol. After chromatography, the title compound (2.09 g) was found to be homogeneous by thin layer chromatography (10% by volume of methylene chloride/hexane on silica gel plates).

¹H NMR (CDCl₃): δ8.13(m, 2H); 7.47(m, 2H); 7.30(d, J=8 Hz, 1H); 6.50(d, J=8 Hz, 1H); 4.00(t, 2H); 3.55(t, 2H); and 2.27(quintet, 2H).

EXAMPLE 9

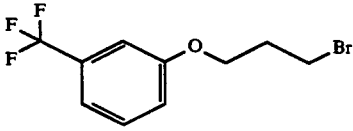

The title compound was prepared and worked up according to the method of Example 6 using 3-trifluoromethylphenol (1.62 g) in place of 3,4-dichlorophenol. After chromatography, the title compound (1.24 g) was found to be homogeneous by thin layer chromatography (10% by volume of methylene chloride/hexane on silica gel plates).

¹H NMR (CDCl₃): δ7.40-6.93(m, 4H); 4.10(t, 2H); 3.57(t, 2H); and 2.30(quintet, 2H).

EXAMPLE 10

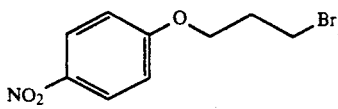

The title compound was prepared and worked up according to the method of Example 6 using 4-nitrophenol (1.39 g) in place of 3,4-dichlorophenol. After chromatography, the title compound (1.67 g) was found to be homogeneous by thin layer chromatography (10% or 20% by volume of ethyl acetate/hexane on silica gel plates).

¹H NMR (CDCl₃): δ8.16(d, 2H); 6.94(d, 2H); 4.22(t, 2H); 3.62 (t, 2H); and 2.37(quintet, 2H).

EXAMPLE 11

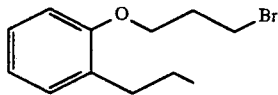

The title compound was prepared by the method of Example 6 using 2-propylphenol (1.36 g) in place of 3,4-dichlorophenol. After chromatography, the title compound (1.59 g) was found to be homogeneous by thin layer chromatography (5% by volume of toluene/hexane on silica gel plates).

¹H NMR (CDCl₃): δ7.23-6.70(m, 4H); 4.07(t, 2H); 3.60(t, 2H); 2.60(t, 2H); 2.32(quintet, 2H); 1.55(m, 2H); and 0.95(t, 3H).

EXAMPLE 12

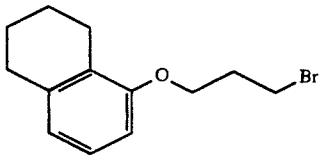

The title compound was prepared by the method of Example 6 using 5,6,7,8-tetrahydro-1-naphthol in place of 3,4-dichlorophenol. After chromatography, the title compound (1.49 g) was found to be homogeneous by thin layer chromatography (10% by volume of methylene chloride/hexane on silica gel plates).

¹H NMR (CDCl₃): δ7.05(dd, J=8 Hz, 1H); 6.68(d, J=8 Hz, 1H); 6.53(d, J=8 Hz, 1H); 4.03(t, 2H); 3.60(t, 2H); 2.68(m, 4H); 2.28(quintet, 2H); and 1.75(m, 4H).

EXAMPLE 13

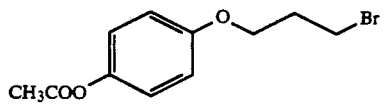

A mixture of 1.52 g (10 mmol) of 4-acetoxyphenol, 2.22 g (11 mmol) 1,3-dibromopropane, and 2.980 g (21 mmol) of anhydrous potassium carbonate in dimethylformamide was stirred rapidly at room temperature for 4 hours. Ethyl acetate was added, and the salts present were removed by filtration. The solvent was removed under reduced pressure, and the residue chromatographed over silica gel. Elution with 15% ethyl acetate-hexane gave 270 mg of the title compound, which was homogeneous by thin layer chromatography (15% by volume of ethyl acetate/hexane on silica gel plates).

¹H NMR (CDCl₃): δ6.87(m, 4H); 4.02(t, 3H); 3.53(t, 2H); 2.33(quintet, 2H); and 2.22(s, 3H).

EXAMPLE 14

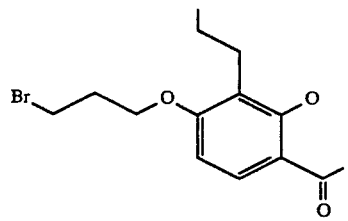

The title compound was prepared and worked up by the method of Example 6 using 25.0 g of 2,4-dihydroxy-3-propylacetophenone in place of 3,4-dichlorophenol. After chromatography, the title compound (8.60 g) was found to be homogeneous by thin layer chromatography (10% by volume of ethyl acetate/hexane on silica gel plates).

¹H NMR (CDCl₃): δ7.60(d, 1H); 6.47(d, 1H); 4.19(t, 2H); 3.62(t, 2H); 2.63(t, 2H); 2.56(s, 3H); 2.36(quintet, 2H); 1.57(m, 2H); and 0.94(t, 3H).

EXAMPLE 15

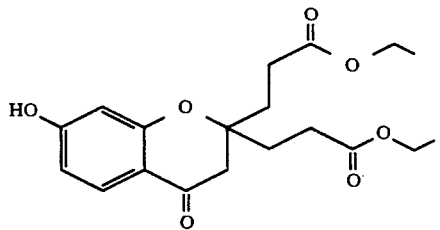

A stirred solution of 4.62 g (30.4 mmol) of 2,4-dihydroxyacetophenone, 7.00 g (30.4 mmol) of diethyl 4-oxopimelate, and 2.2 g (30 mmol) of pyrrolidine in 38 ml of toluene was refluxed under a water separator for 3.5 hours. After the mixture was allowed to cool, it was chromatographed directly over silica gel using ethyl acetate/hexane as eluent to produce 3.82 g of the title compound as a solid, m.p. 108.5°-109.5° C.

¹H NMR (CDCl₃): δ8.30(br s, 1H); 7.76(d, J=8 Hz, 1H); 6.58 (dd, J=8 Hz, J=2Hz, 1H); 6.40(d, J=2 Hz, 1H); 4.20(q, 4H); 2.78(br s, 1H); 2.68-1.98(m, 8H); and 1.32(t, 3H).

Analysis calculated for C₁₉H₂₄O₇(MW=364.40):
Calcd.: C, 62.62; H, 6.64.
Found: C, 62.62; H, 6.39.

EXAMPLE 16 dimethyl 3,4-dihydro-4-oxo-7-(3-phenoxypropoxy)-8-propyl-2H-1-benzopyran-2,2-dipropanoate

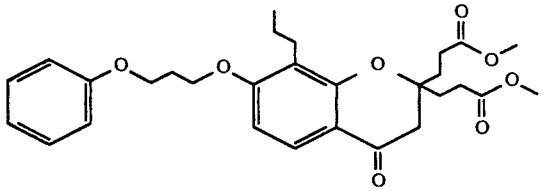

A mixture of 1.00 g (2.65 mmol) of the title diester of Example 2, 684 mg (3.18 mmol) of 3-phenoxy-1-bromopropane, and 769 mg (5.57 mmol) of anhydrous potassium carbonate in 23 ml of dimethylformamide was stirred overnight at room temperature. After removal of solvent under reduced pressure, the residue was partitioned between 75 ml ethyl acetate and 25 ml water, and the aqueous layer separated. The aqueous layer was acidified with 3N hydrochloric acid, and the layer shaken again. The aqueous layer was further extracted with 25 ml ethyl acetate. The combined organic extracts were washed with brine, dried (MgSO4), the drying agent removed by filtration, and the solvent removed on a rotary evaporator. The residue was chromatographed on silica gel using ethyl acetate as eluent. After removal of solvent, the product was crystallized from 3:1 ethyl acetate/hexane to yield 945 mg, m.p. 100°–100.5° C.

Analysis for $C_{29}H_{36}O_8$ (MW = 512.61):
Calcd.: C, 67.95; H, 7.08.
Found: C, 68.00; H, 7.11.

EXAMPLE 17

3,4-dihydro-4-oxo-7-(3-phenoxypropoxy)-8-propyl-2H-1-benzopyran-2,2-dipropanoic acid

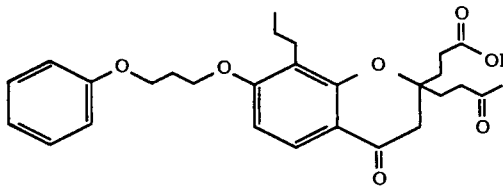

A mixture of 611 mg (1.19 mmol) of the title product of Example 16, 0.72 ml of 50% aqueous sodium hydroxide, and 11.7 ml of water was stirred at reflux. After one hour, another 2 ml of water was added and the reaction mixture was heated for an additional 2 hours. The mixture was allowed to cool and then partitioned between 75 ml of ethyl acetate and 50 ml of 3N hydrochloric acid. The aqueous layer was further extracted twice with 25 ml aliquots of ethyl acetate. The combined organic extracts were washed with water, with brine, dried over magnesium sulfate, filtered, and solvent removed on a rotary evaporator to give 501 mg of title product, m.p. 161.5°–162° C.

Analysis for $C_{27}H_{32}O_8$ (MW = 484.55):
Calcd.: C, 66.92; H, 6.66.
Found: C, 67.10; H, 6.70.

EXAMPLE 18 dimethyl 3,4-dihydro-4-oxo-7-(phenylmethoxy)-8-propyl-2H-1-benzopyran-2,2-dipropanoate

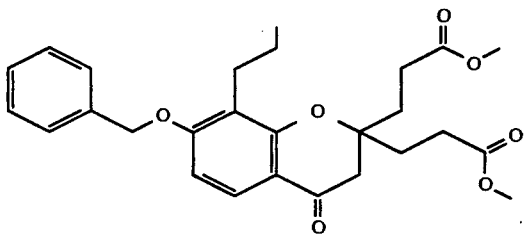

A mixture of 378 mg (1.00 mmol) of the title product of Example 2, 190 mg (1.1 mmol) of benzyl bromide, and 290 mg (2.10 mmol) of anhydrous potassium carbonate in 10 ml of dimethylformamide was stirred at room temperature for 60 hours. The solvent was removed under reduced pressure, and the residue was partitioned between ethyl acetate and 3N hydrochloric acid. The aqueous layer was extracted with ethyl acetate. The combined organic extracts were dried over magnesium sulfate, the drying agent removed by filtration, and the solvent removed under reduced pressure. After flash chromatography on silica gel using 40% by volume of ethyl acetate/hexane as eluent, there was obtained 0.43 g of the title product as an oil.

$^1$H NMR (CDCl₃): δ7.69(d, 1H); 7.40(br s, 5H); 6.59 (d, 1H); 5.11(s, 2H); 3.65(s, 6H); 2.64(br s, 2H); and 0.94(t, 3H).

Analysis for $C_{27}H_{32}O_7$ (MW = 468.55):
Calcd.: C, 69.21; H, 6.88.
Found: C, 69.17; H, 6.91

EXAMPLE 19 dimethyl 7-[3-[4-(acetyloxy)phenoxy]propoxy]-3-4-dihydro-4-oxo-8-propyl-2H-1-benzopyran-2,2-dipropanoate

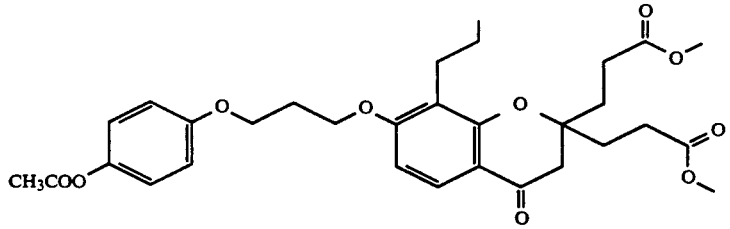

The title compound (660 mg), isolated as the ¼ hydrate, was prepared by the method of Example 18 substituting the title product (380 mg, 1.43 mmol) of Example 13 for benzyl bromide.

$^1$H NMR (CDCl₃): δ7.70(d, 1H); 6.99(d, 2H); 6.79(d, 2H); 6.54 (d, 1H); 4.19(t, 2H); 4.13(t, 2H); 3.63(s, 6H); 2.64(br s, 2H); 2.25(s, 3H); and 0.91(t, 3H).

Analysis for $C_{31}H_{38}O_{10}·\frac{1}{4}H_2O$ (MW = 570.64):
Calcd.: C, 64.72; H, 6.75.
Found: C, 64.69; H, 6.84.

EXAMPLE 20

3,4-dihydro-7-[3-(4-hydroxyphenoxy)propoxy]-4-oxo-
8-propyl-2H-1-benzopyran-2,2-dipropanoic acid

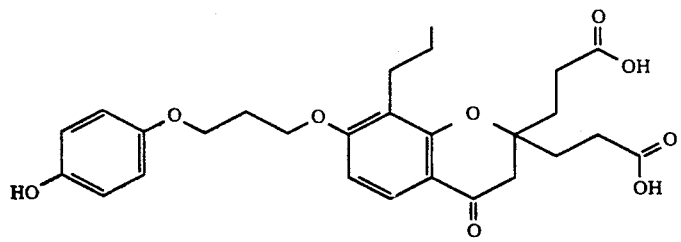

The title product of Example 19 (500 mg, 0.876 mmol) was stirred in 14 ml of methanol containing 0.85 ml of a 50% aqueous solution of sodium hydroxide for one hour. The mixture was partitioned between 40 ml of ethyl acetate and 30 ml of 3N hydrochloric acid, and the aqueous layer further extracted twice with 20 ml aliquots of ethyl acetate. The combined organic extracts were washed with brine, dried over magnesium sulfate (MgSO$_4$), the drying agent removed by filtration, and the solvent removed on a rotary evaporator. Crystallization of the residue from diethyl ether gave the title product (321 mg), m.p. 160°–166° C.

Analysis for C$_{27}$H$_{32}$O$_9$ (MW=500.55):
Calcd.: C, 64.78; H, 6.44.
Found: C, 64.59; H, 6.84.

EXAMPLE 21 diethyl 3,4-dihydro-7-[3-(4-chlorophenoxy)propoxy]-4-oxo-
8-propyl-2H-1-benzopyran-2,2-dipropanoate

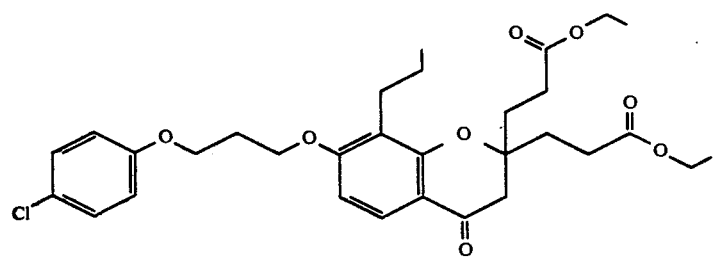

The title compound (620 mg) was prepared by the method of Example 18 substituting the title product of Example 1 (512 mg) for the title product of Example 2, and substituting the title product of Example 3 (355 mg) for benzyl bromide.

$^1$H NMR (CDCl$_3$): δ7.70(d, 1H); 7.20(d, 2H); 6.79(d, 2H); 6.54 (d, 1H); 4.09(q, (4H); 2.64(br s, 2H); 1.23(t, 6H); and 0.91(t, 3H).

EXAMPLE 22

7-[3-(4-chlorophenoxy)propoxy]-3,4-dihydro-4-oxo-
8-propyl-2H-1-benzopyran-2,2-dipropanoic acid

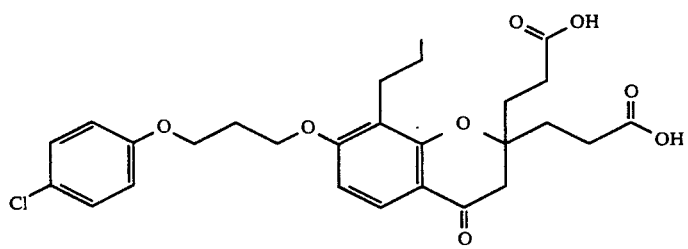

The title compound (510 mg), m.p. 133°–134° C., was prepared by the method of Example 20 substituting the title product of Example 21 (620 mg) instead of the title product of Example 19, and carrying out the reaction for one hour at reflux instead of for two hours at room temperature.

Analysis for C$_{27}$H$_{31}$ClO$_8$ (MW=519.00):
Calcd.: C, 62.49; H, 6.02; Cl, 6.83.
Found: C, 62.42; H, 5.81; Cl, 7.78.

EXAMPLE 23 diethyl 3,4-dihydro-7-[3-(2-naphthalenyloxy)propoxy]-4-oxo-
8-propyl-2H-1-benzopyran-2,2-dipropanoate

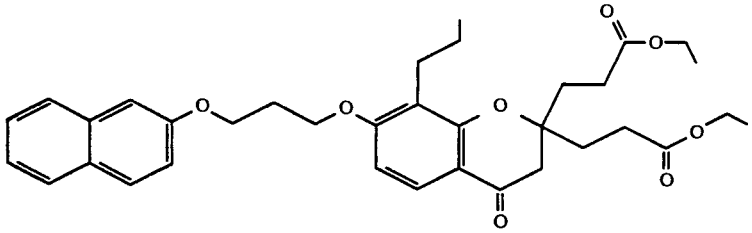

The title compound (569 mg) was prepared by the method of Example 19 substituting the 406 mg of title product of Example 1 for the title product of Example 2, and further substituting the 299 mg of title product of Example 4 for benzyl bromide.

$^1$H NMR (CDCl$_3$): δ7.78–6.96(m, 7H); 7.70(d, 1H); 6.56(d, 1H); 4.09 (q, 4H); 2.64(br s, 2H); 1.23(t, 6H); and 0.93(t, 3H).

EXAMPLE 24

3,4-dihydro-7-[3-(2-naphthalenyloxy)propoxy]-4-oxo-8-propyl-2H-1-benzopyran-2,2-dipropanoic acid

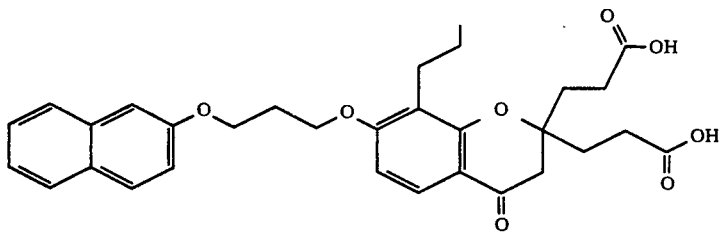

The title compound was prepared by the method of Example 22 substituting 539 mg of the title product of Example 23 for the title product of Example 21. Crystallization from 5:1 ethyl acetate:hexane yielded 303 mg, m.p. 157.5°–158° C.

Analysis for C$_{31}$H$_{34}$O$_8$ (MW=534.61):
Calcd.: C, 69.64; H, 6.41.
Found: C, 69.49; H, 6.25.

EXAMPLE 25

3,4-dihydro-4-oxo-7-(phenylmethoxy)-8-propyl-2H-1-benzopyran-2,2-dipropanoic acid

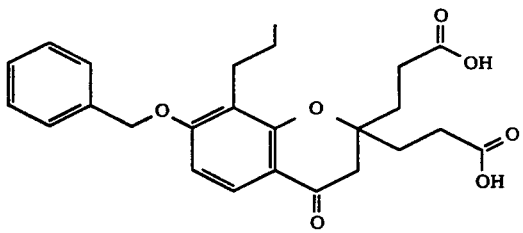

The title compound, 102 mg, m.p. 202°–205° C., was prepared by the method of Example 22 substituting the title product of Example 18 (455 mg) for the title product of Example 21, and utilizing methylene chloride as the extraction solvent instead of ethyl acetate.

Analysis for C$_{25}$H$_{28}$O$_7$ (MW=440.50):
Calcd.: C, 68.17; H, 6.41.
Found: C, 67.83; H, 6.25.

EXAMPLE 26 diethyl 3,4-dihydro-4-oxo-7-(3-phenoxypropoxyl)-2H-1-benzopyran-2,2-dipropanoate

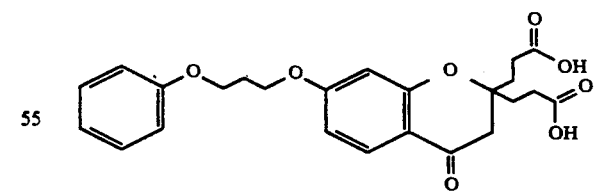

The title compound (500 mg) was prepared by the method of Example 16 substituting the title product of Example 15 (364 mg) for the title product of Example 2.

$^1$H NMR (CDCl$_3$): δ7.74(d, J=8 Hz, 1H); 7.36–6.78(m, 5H); 6.53 (dd, J=8 Hz, 1H); 6.34(d, J=2 Hz, 1H); 4.09(q, 4H); 2.64(br s, 2H); and 1.23(t, 6H).

EXAMPLE 27

3,4-dihydro-4-oxo-7-(3-phenoxypropoxy)-2H-1-benzopyran-2,2-dipropanoic acid

The title compound was prepared by the method of Example 22 substituting the title product of Example 26 for the title product of Example 21. Crystallization from 60% by volume ethyl acetate/hexane yielded 219 mg, m.p. 132.5°–133° C.

Analysis for C$_{24}$H$_{26}$O$_8$ (MW=442.47):
Calcd.: C, 65.15; H, 5.92.
Found: C, 64.86; H, 5.77.

EXAMPLE 28 diethyl 3,4-dihydro-7-[3-(1-naphthalenyloxy)propoxy]-4-oxo-8-propyl-2H-1-benzopyran-2,2-dipropanoate

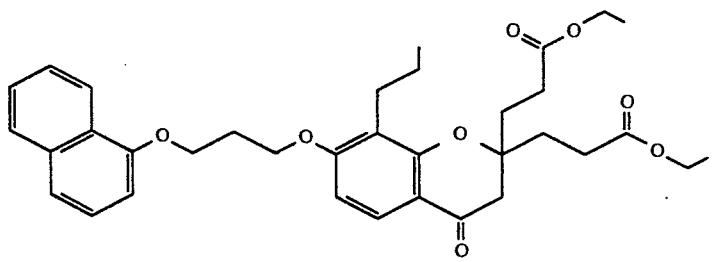

The title compound (549 mg) was prepared by the method of Example 18 substituting the title product of Example 1 (406 mg) for the title product of Example 2, and further substituting the title product of Example 5 (299 mg) for benzylbromide.

¹H NMR (CDCl₃): δ8.28–6.71(m, 7H); 7.70(d, 1H); 6.56(d, 1H); 4.09(q, 4H); 2.63(br s, 2H); 1.23(t, 6H); and 0.93(t, 3H).

EXAMPLE 29

3,4-dihydro-7-[3-(1-naphthalenyloxy)propoxy]-4-oxo-8-propyl-2H-1-benzopyran-2,2-dipropanoic acid

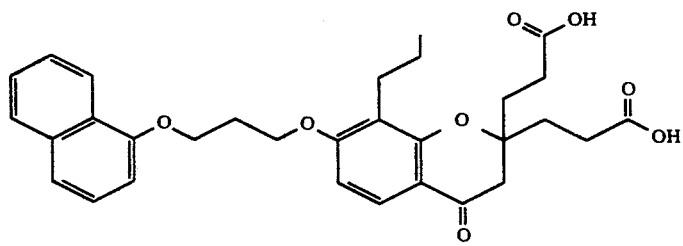

The title compound was prepared by the method of Example 22 substituting the title product of Example 28 (549 mg) for the title product of Example 21 to give, after crystallization from ethyl acetate, 141 mg, m.p. 164°–167° C.

Analysis for $C_{31}H_{34}O_8$ (MW=534.61):
Calcd.: C, 69.64; H, 6.41.
Found: C, 69.64; H, 6.47.

EXAMPLE 30 diethyl 7-[3-(3,4-dichlorophenoxy)propoxy]-3,4-dihydro-4-oxo-8-propyl-2H-1-benzopyran-2,2-dipropanoate

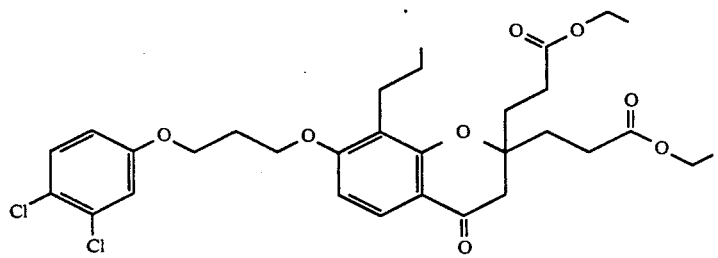

The title compound (370 mg) was prepared by the method of Example 18 substituting 266 mg of the title product of Example 1 for the title product of Example 2, and further substituting 211 mg of the title product of Example 6 for benzyl bromide.

EXAMPLE 31

7-[3-(3,4-dichlorophenoxy)propoxy]-3,4-dihydro-4-oxo-8-propyl-2H-1-benzopyran-2,2-dipropanoic acid

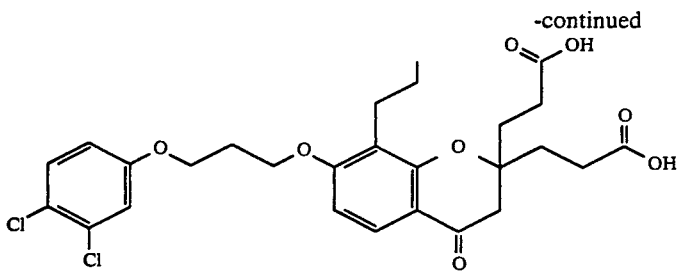

The title compound, isolated as the hemihydrate, was prepared by the method of example 22 substituting the title product of Example 30 (370 mg) for the title product of Example 21 to give, after trituration with methylene chloride, 174 mg, m.p. 136.5°-137° C.

Analysis for $C_{27}H_{30}Cl_2O_8 \cdot \frac{1}{2}H_2O$ (MW=562.45):
Calcd.: C, 57.65; H, 5.56; Cl, 12.61.
Found: C, 57.62; H, 5.66; Cl, 12.77.

EXAMPLE 32 diethyl 7-[3-(4-bromophenoxy)propoxy]-3,4-dihydro-4-oxo-8-propyl-2H-1-benzopyran-2,2-dipropanoate

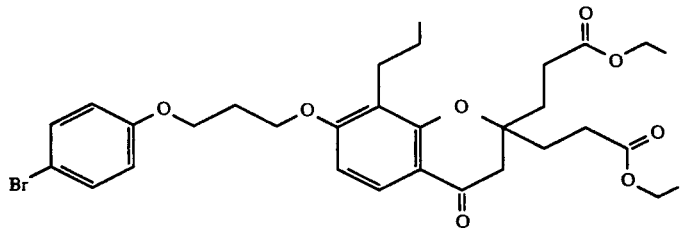

The title product (440 mg) was prepared by the method of Example 18, substituting the title product of Example 1 (406 mg) for the title product of Example 2, and further substituting the title product of Example 7 (353 mg) for benzyl bromide.

$^1$H NMR (CDCl$_3$): δ7.69(d, 1H); 7.35(d, 2H); 6.74(d, 2H); 6.54 (d, 1H); 4.09(q, 4H); 2.64(br s, 2H); 1.23(t, 6H); and 0.91(t, 3H).

EXAMPLE 33

7-[3-(4-bromophenoxy)propoxy]-3,4-dihydro-4-oxo-8-propyl-2H-1-benzopyran-2,2-dipropanoic acid

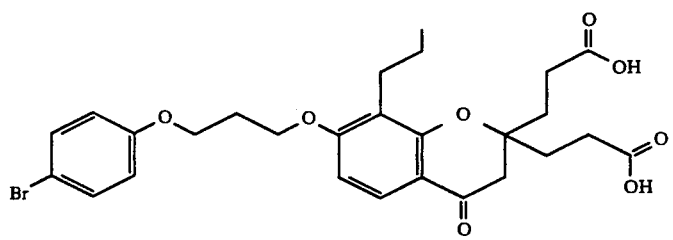

The title product, isolated as the hydrate, was prepared by the method of Example 22 substituting the title product of Example 32 for the title product of Example 21 to give, after crystallization from ethyl acetate/hexane, 278 mg, m.p. 136°-136.5° C.

Analysis for $C_{27}H_{31}BrO_8 \cdot H_2O$ (MW=581.45):
Calcd.: C, 57.35; H, 5.54; Br, 14.60.
Found: C, 57.42; H, 5.54; Br, 14.70.

EXAMPLE 34 diethyl 7-[3-[(4-chloro-1-naphthalenyl)oxy]propoxy]-3,4-dihydro-4-oxo-8-propyl-2H-1-benzopyran-2,2-dipropanoate

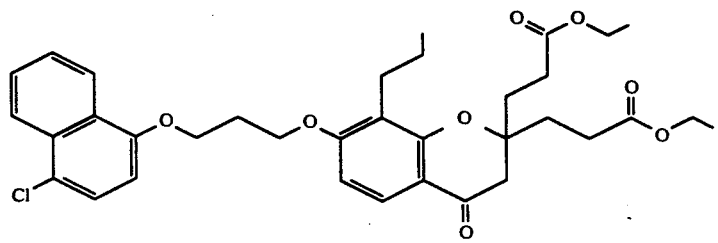

The title compound (525 mg) was prepared by the method of Example 18 substituting the title product of Example 1 (406 mg) for the title product of Example 2, and further substituting the title product of Example 8 (360 mg) for benzyl bromide.

¹H NMR (CDCl₃): δ8.21(m, 2H); 7.70(d, 1H); 7.59(m, 2H): 743(d, 1H); 6.71(d, 1H); 6.56(d, 1H): 4.09(q, 4H): 2.63(br s, 2H); 1.23(t, 6H); and 0.91(t, 3H).

EXAMPLE 35

7-[3-[(4-chloro-1-naphthalenyl)oxy]propoxy]-3,4-dihydro-4-oxo-8-propyl-2H-1-benzopyran-2,2-dipropanoic acid

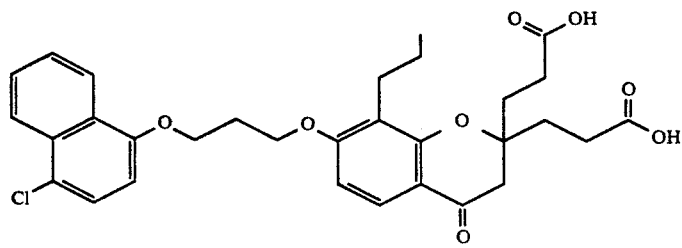

The title compound was prepared by the method of Example 22 substituting the title product of Example 34 (515 mg) for the title product of Example 21 to give, after trituration with diethylether, 325 mg as a solid, m.p. 170.5°–171° C.

Analysis for $C_{31}H_{33}ClO_8$ (MW=569.06):
Calcd.: C, 65.42; H, 5.84; Cl, 6.23.
Found: C, 65.31; H, 5.77; Cl, 6.22.

EXAMPLE 36 diethyl 3,4-dihydro-4-oxo-8-propyl-7-[3-[3-(trifluoromethyl)phenoxy]propoxy]-2H-1-benzopyran-2,2-dipropanoate

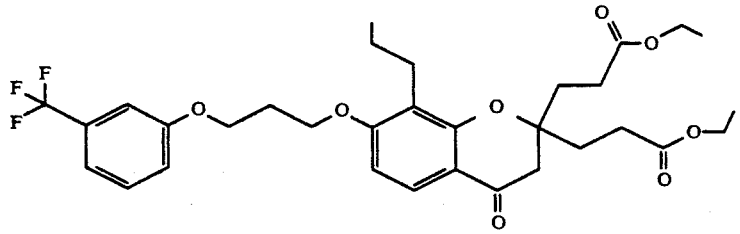

The title compound (497 mg) was prepared by the method of Example 18 substituting the product of Example 1 (406 mg) for the product of Example 2, and further substituting the product of Example 9 for benzyl bromide.

¹H NMR (CDCl₃): δ7.70(d, 1H); 7.48–6.90(m, 3H); 6.54(d, 1H); 4.09(q, 4H); 2.63(br s, 2H); 1.23(t, 6H); and 0.90(t, 3H).

EXAMPLE 37

3,4-dihydro-4-oxo-8-propyl-7-[3-[3-(trifluoromethyl)phenoxy]propoxy]-2H-1-benzopyran-2,2-dipropanoic acid

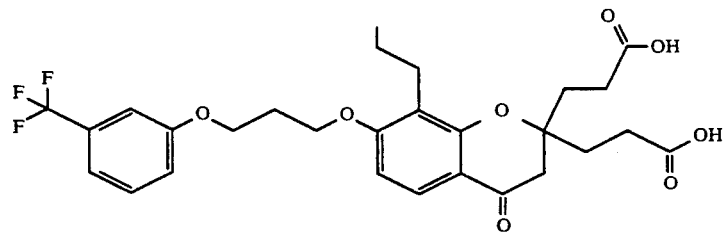

The title compound was prepared by the method of Example 22 except that the title product of Example 36 (487 mg) was substituted for the title product of Example 21. Trituration with diethyl ether produced 267 mg of the titled compound as a solid, m.p. 129°–129.5° C.

Analysis for $C_{28}H_{31}F_3O_8$ (MW=552.55):
Calcd.: C, 60.86; H, 5.66.
Found: C, 60.74; H, 5.56.

EXAMPLE 38 diethyl 3,4-dihydro-7-[3-(4-nitrophenoxy)propoxy]-4-oxo-8-propyl-2H-1-benzopyran-2,2-dipropanoate -continued

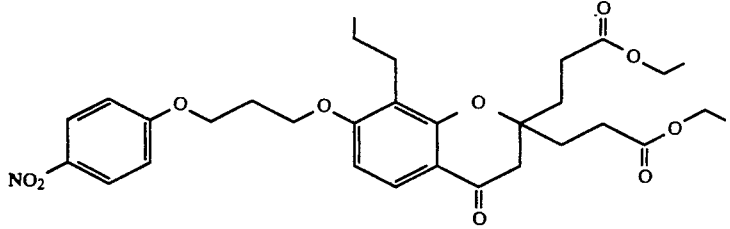

The title product (470 mg) was prepared by the method of Example 18 substituting 406 mg of the product of Example 1 for the product of Example 2, and further substituting 312 mg of the title product of Example 10 for benzyl bromide.

$^1$H NMR (CDCl$_3$): δ8.16(d, 2H); 7.70(d, 1H); 6.94 (d, 2H); 6.54(d, 1H); 4.09(q, 4H); 2.65(br s, 2H); 1.24(t, 6H); and 0.91(t, 3H).

EXAMPLE 39

3,4-dihydro-7-[3-(4-nitrophenoxy)propoxy]-4-oxo-8-propyl-2H-1-benzopyran-2,2-dipropanoic acid

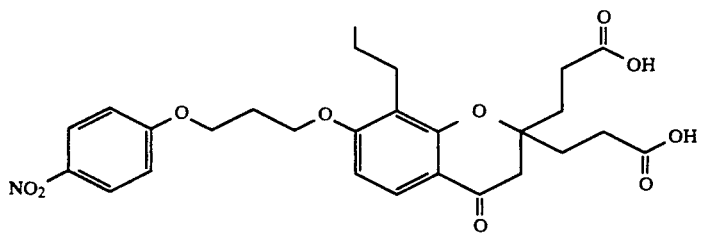

The title compound was prepared by the method of Example 22 substituting the title product of Example 38 (110 mg) for the title product of Example 21. Trituration with ethyl acetate/hexane produced 46 mg of the titled compound as a solid, m.p. 171.5°–172° C.

Analysis for C$_{27}$H$_{31}$NO$_{10}$ (MW=529.55):
Calcd.: C, 61.23; H, 5.90; N, 2.65.
Found: C, 60.97; H, 5.78; N, 2.39.

EXAMPLE 40 diethyl 3,4-dihydro-7-[3-(2-propylphenoxy)propoxy]-4-oxo-8-propyl-2H-1-benzopyran-2,2-dipropanoate

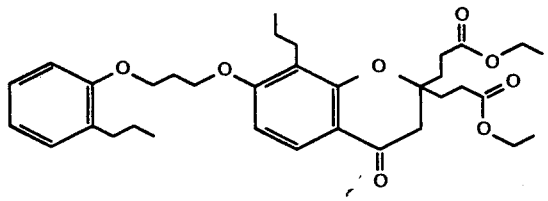

The title compound (471 mg) was prepared by the method of Example 18 except that the title product of Example 1 (406 mg) was used instead of the title product of Example 2, and the title product of Example 11 (308 mg) was used instead of benzyl bromide.

$^1$H NMR (CDCl$_3$): δ7.70(d, 1H); 7.16–6.69(m, 4H); 6.55(d, 1H); 4.09(q, 4H); 2.63(br s, 2H); 1.21(t, 6H); and 0.90(t, 6H).

EXAMPLE 41

3,4-dihydro-7-[3-(2-propylphenoxy)propoxy]-4-oxo-8-propyl-2H-1-benzopyran-2,2-dipropanoic acid

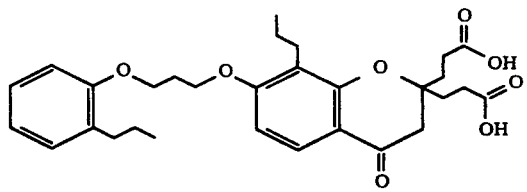

The title compound was prepared by the method of Example 22 substituting the title product of Example 40 (446 mg) for the title product of Example 21. Crystallization from ethyl acetate/hexane produced 252 mg as a solid, m.p. 163°–165° C.

Analysis for C$_{30}$H$_{38}$O$_8$ (MW=526.63):
Calcd.: C, 68.42; H, 7.27.
Found: C, 68.06; H, 7.18.

EXAMPLE 42 diethyl 3,4-dihydro-4-oxo-8-propyl-7-[3-[(5,6,7,8-tetrahydro-1-naphthalenyl)oxy]propoxy]-2H-1-benzopyran-2,2-dipropanoate -continued

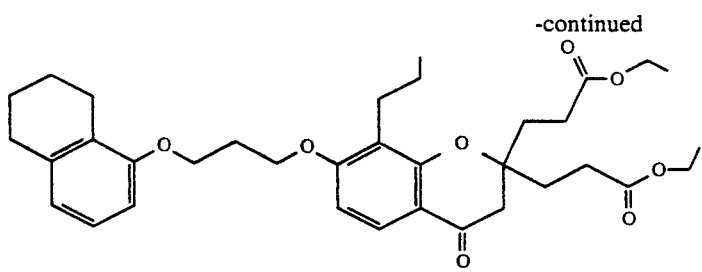

The title compound (460 mg) was prepared by the method of Example 18 substituting the title product of Example 1 (406 mg) for the title product of Example 2, and further substituting the title product of Example 12 (323 mg) for benzyl bromide. Crystallization from ethyl acetate gives the analytically pure title compound, m.p. 87.5°-88° C.

Analysis for $C_{35}H_{46}O_8$ (MW=594.75):
Calcd.: C, 70.68; H, 7.80.
Found: C, 70.72; H, 7.94.

$^1$H NMR (CDCl$_3$): δ7.69(d, 1H); 7.00(dd, 1H); 6.63(d, 1H); 6.60(d, 1H); 6.54(d, 1H); 4.09(q, 4H); 2.64(br s, 2H); 1.24(t, 6H); and 0.91(t, 3H).

EXAMPLE 43

3,4-dihydro-4-oxo-8-propyl-7-[3-[(5,6,7,8-tetrahydro-1-naphthalenyl)oxy]propoxy]-2H-1-benzopyran-2,2-dipropanoic acid

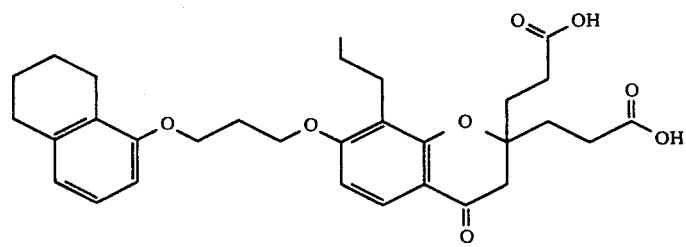

The title compound was prepared by the method of Example 22 substituting the title product of Example 42 (445 mg) for the title product of Example 21. Trituration with ethyl acetate produced 317 mg of the titled compound as a solid, m.p. 126.5°-127.5° C.

Analysis for $C_{31}H_{38}O_8$ (MW=538.64):
Calcd.: C, 69.12; H, 7.11.
Found: C, 69.14; H, 7.24.

EXAMPLE 44 diethyl 3,4-dihydro-8-propyl-7-hydroxy-2H-1-benzopyran-2,2-dipropanoate

-continued

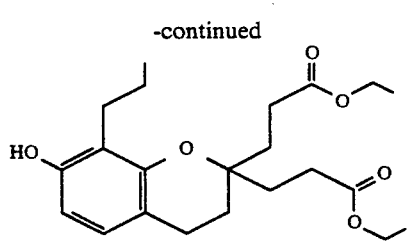

The title product of Example 1 (4.19 g, 10.3 mmol) was dissolved in 50 ml of acetic acid, and then hydrogenated at 70° C. using 60 psi of hydrogen and 10% palladium on carbon as catalyst. After eight hours, the mixture was allowed to cool, and insolubles were removed by filtration. The filtrate was concentrated under reduced pressure. The residue was chromatographed on silicagel column. Elution with 20% ethyl acetate/hexane afforded the title compound (0.80 g).

$^1$H NMR (CDCl$_3$): δ6.67(d, 1H); 6.27(d, 1H); 5.47(br s, 1H); 4.10(q, 4H); 2.82-2.23(m, 8H); 2.10-1.40(m, 8H); 1.20(t, 6H); and 0.92(t, 3H).

IR: One carboxyl absorption at 1718 cm$^{-1}$.

EXAMPLE 45 bis(2,3-dihydroxypropyl) 3,4-dihydro-4-oxo-7-(3-phenoxypropoxy)-8-propyl-2H-1-benzopyran-2,2-dipropanoate

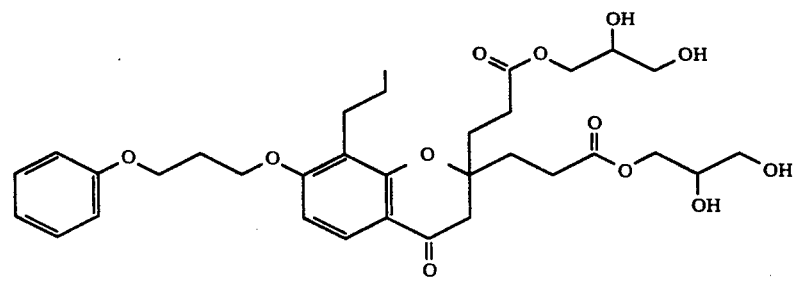

A mixture of 250 mg (0.515 mmol) of the titled product of Example 17, 153 mg (2.06 mmol) of glycidol, and 9 mg of a 40% solution of benzyl-trimethylammonium hydroxide in methanol in 2.5 ml of dimethyl formamide under argon was stirred overnight at 70° C. After addition of another 153 mg of glycidol and one drop of 40% methanolic benzyltrimethylammonium hydroxide, the temperature was raised to 85°–90° C. with stirring. After stirring for 7 hours, the mixture was permitted to cool and was then partitioned between ethyl acetate and water. The aqueous layer was further extracted twice with ethyl acetate. The combined organic extracts were washed with brine, dried ($Na_2SO_4$), the drying agent removed by filtration, and the solvent removed on a rotary evaporator. The residue was chromatographed on a silica gel column. Elution with 10% methanol/2.5% acetic acid/87.5% ethyl acetate as eluent afforded, after drying under vacuum for eight hours, the title product (170 mg), which was isolated as the hemihydrate.

Analysis for $C_{33}H_{44}O_{12} \cdot \frac{1}{2}H_2O$ (MW=641.72):
Calcd.: C, 61.77; H, 7.07.
Found: C, 61.73; H, 6.99.

EXAMPLE 46 bis[2-(phenylmethoxy)-1-[(phenylmethoxy)methyl]ethyl] 3,4-dihydro-4-oxo-8-propyl-7-[3-[(5,6,7,8-tetrahydro-1-naphthalenyl)oxy]propoxy]-2H-1-benzopyran-2,2-dipropanoate

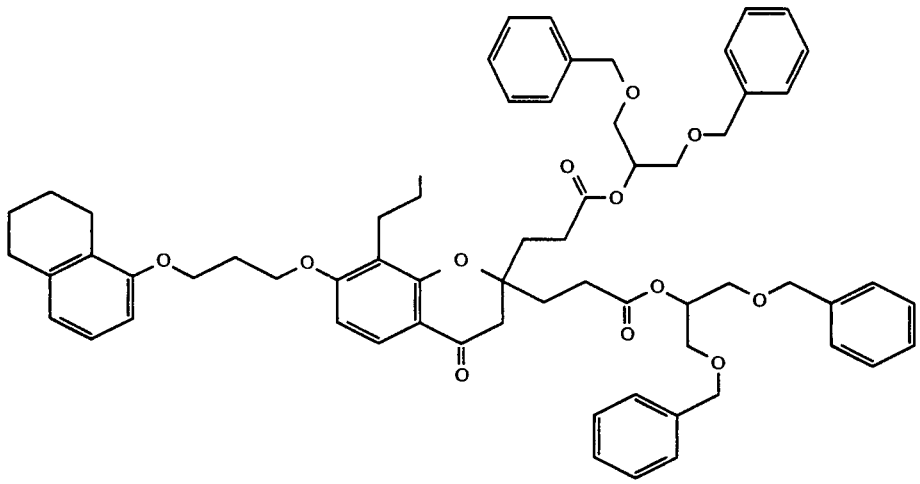

A mixture of 500 mg (0.928 mmol) of the titled product of Example 43 and 0.5 ml of thionyl chloride in 10 ml of benzene was stirred at reflux at 1.5 hours. The mixture was allowed to cool, and the solvent was removed under reduced pressure. The residue was dissolved in 4 ml of methylene chloride ($CH_2Cl_2$), a solution of 1.19 g (4.38 mmol) of 1,3-dibenzyloxy-2-propanol in 2 ml of methylene chloride and 2 ml of pyridine was added, and the mixture was stirred at room temperature for three days. To the mixture was added 50 ml of diethyl ether, and the resulting mixture washed successively with dilute hydrochloric acid, with water, and with brine. The solution was dried over magnesium sulfate, the drying agent removed by filtration, and the solvent was removed on a rotary evaporator. Chromatography over a silica gel column using a solvent gradient of 20% increasing to 50% of ethyl acetate/hexane gave 373 mg of the title compound.

Analysis for $C_{65}H_{74}O_{12}$ (MW=1047.31):
Calcd.: C, 74.57; H, 7.12.
Found: C, 74.51; H, 7.19.
$^1H$ NMR ($CDCl_3$): δ7.71(d, 1H); 7.28(m, 20H); 7.04(dd, 1H); 6.69(d, 1H); 6.63(d, 1H); 6.56(d, 1H); 5.18(quintet, 2H); 4.49(s, 8H); 4.22(t, 2H); 4.13 (t, 2H); 3.60(d, 8H); 2.73(br s, 2H); 2.62(m, 4H); 2.53(t, 2H); 2.28(quintet, 2H): 2.04(t, 4H); 1.75(m, 4H); 1.48(m, 2H); and 0.89(t, 3H).

EXAMPLE 47 bis[2-hydroxy-1-(hydroxymethyl)ethyl] 3,4-dihydro-4-oxo-8-propyl-7-[3-[(5,6,7,8-tetrahydro-1-naphthalenyl)oxy]propoxy]-2H-1-benzopyran-2,2-dipropanoate

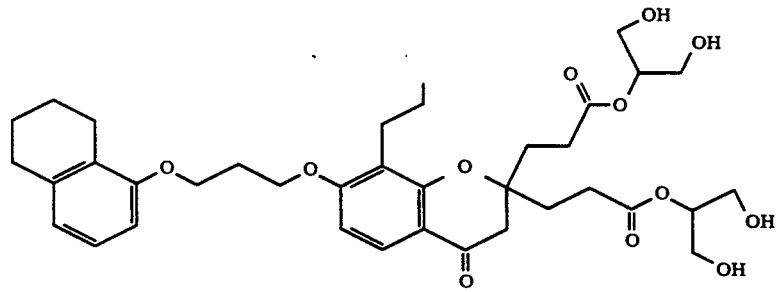

The titled product of Example 46 (0.258 g, 0.246 mmol) was dissolved in 25 ml of tetrahydrofuran, and then hydrogenated at room temperature using hydrogen at atmospheric pressure and 10% palladium on carbon (Pd/C) as catalyst. The insolubles were removed by filtration, and the solvent removed under reduced pressure. The residue was chromatographed on silica gel column. Elution with 5% methanol/ethyl acetate afforded 125 mg of the title compound.

Analysis for $C_{37}H_{50}O_{12}$ (MW=686.80):
Calcd.: C, 64.71; H, 7.35.
Found: C, 64.35; H, 7.41.

EXAMPLE 48 diethy 7-[3-(4-aminophenoxy)propoxy]-3,4-dihydro-4-oxo-8-propyl-2H-1-benzopyran-2,2-dipropanoate

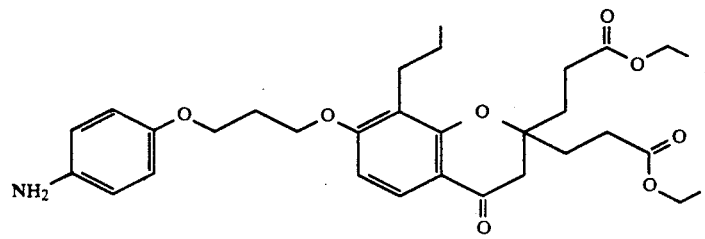

A solution of 363 mg (0.62 mmol) of the title product of Example 38 in 45 ml of ethanol was treated with 36 mg of Raney nickel and then hydrogenated at atmospheric pressure and room temperature for 3.25 hr. The reaction mixture was filtered and the solvent was removed under reduced pressure. Chromatography of the residue over silica gel using 50—50 ethyl acetate/hexane as eluent gave the title compound as a white solid, m.p. 125.5°–127° C.

Analysis for $C_{31}H_{41}O_8$ (MW=555.68):
Calcd.: C, 67.00; H, 7.44; N, 2.52.
Found: C, 67.43; H, 7.29; N, 2.09.

EXAMPLE 49

3,4-dihydro-N,N,N,N-tetraethyl-4-oxo-8-propyl-7-[3-[(5,6,7,8-tetrahydro-1-naphthalenyl)oxy]propoxy]-2H-1-benzopyran-2,2-dipropanamide

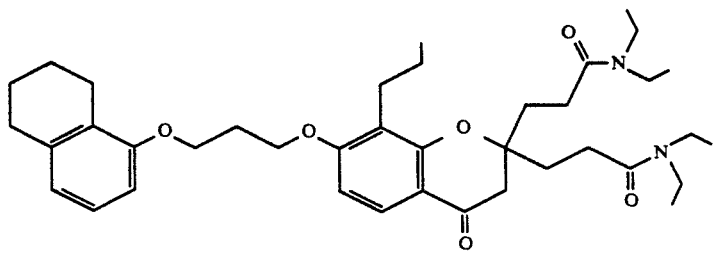

A mixture of 500 mg (0.928 mmol) of the titled product of Example 43 and 1 ml of thionyl chloride was stirred at reflux for 1.5 hours. The mixture was permitted to cool, and the volatile components removed under reduced pressure. The residue was dissolved in benzene, and 1 ml of diethylamine was added. After stirring for 2 hours, the reaction mixture was washed with 3N hydrochloric acid and with water. The solution was dried (MgSO4), the drying agent removed by filtration, and solvent removed on a rotary evaporator. The residue was chromatographed on a silica gel column. Elution with 5% methanol/methylene chloride gave the titled compound (214 mg) as an oil.

Analysis for $C_{39}H_{56}N_2O_6$ (MW=648.89):
Calcd.: C, 72.18; H, 8.70; N, 4.32.
Found: C, 72.29; H, 8.85; N, 4.26.

EXAMPLE 50

3,4-dihydro-4-oxo-8-propyl-7-[3-[(5,6,7,8-tetrahydro-1-naphthalenyl)oxy]propoxy]-2H-1-benzopyran-2,2-dipropanoic acid monoethyl ester

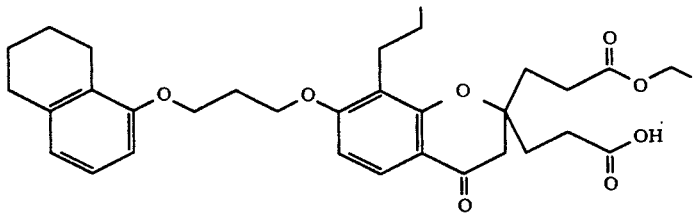

To a solution of the titled product of Example 43 (676 mg, 1.25 mmol) in 5 ml of dimethylformamide (DMF) was added 190 mg (1.25 mmol) of 1,8-diazabicyclo (5.4.0) undec-7-ene followed by 585 mg (3.75 mmol) of iodoethane. After stirring overnight at room temperature, the solvent was removed under reduced pressure. The residue was dissolved in CH2Cl2. The solution was then washed with 3N hydrochloric acid, dried (Na₂SO₄), filtered, and the solvent removed on a rotary evaporator. The residue was chromatographed on a silica gel column. Elution with 35% ethyl acetate/61.5% hexane/2.5% acetic acid as eluent produced the title product which was crystallized from 3:1 hexane:ethyl acetate to give 183 mg, m.p. 83.5°-84.5° C.

Analysis for C₃₃H₄₂O₈ (MW=566.70):
Calcd.: C, 69.95; H, 7.47.
Found: C, 69.83; H, 7.58.

EXAMPLE 51 methyl 3,4-dihydro-4-oxo-2-(3-oxo-3-[1-pyrrolidinyl]propyl)-8-propyl-7-[3-[(5,6,7,8-tetrahydro-1-naphthalenyl)oxy]propoxy]-2H-1-benzopyran-2-propanoate

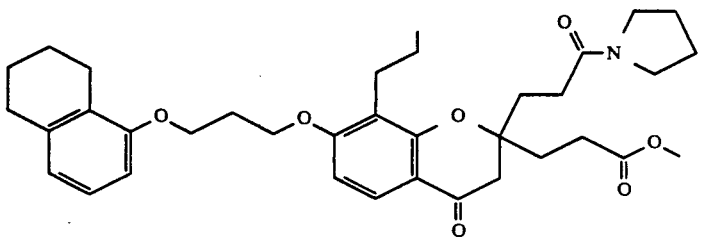

A mixture of 500 mg (1.20 mmol) of the title amide-ester of Example 2, 483 mg (1.8 mmol) of the title product of Example 12, and 348 mg (2.52 mmol) of anhydrous potassium carbonate in 12 ml of dimethylformamide was stirred at 90° C. (oil bath) for three hours. The mixture was permitted to cool, and the solvent was removed under reduced pressure. The residue was partitioned between ethyl acetate and water, and the aqueous layer was further extracted with two portions of ethyl acetate. The combined organic extracts were washed with brine, dried over sodium sulfate, filtered, and the solvent removed under reduced pressure. Chromatography of the residue over silica gel, using methanol-methylene chloride as eluent, gave a solid which was triturated with diethyl ether to give the title compound (468 mg), m.p. 105°-107° C.

Analysis for C₃₆H₄₇NO₇ (MW=605.78):
Calcd.: C, 71.38; H, 7.82; N, 2.31.
Found: C, 71.36; H, 8.00; N, 2.29.

EXAMPLE 52

3,4-dihydro-4-oxo-2-[3-oxo-3-(1-pyrrolidinyl)propyl]-8-propyl-7-[3-[(5,6,7,8-tetrahydro-1-naphthalenyl)oxy]propoxy]-2H-1-benzopyran-2-propanoic acid

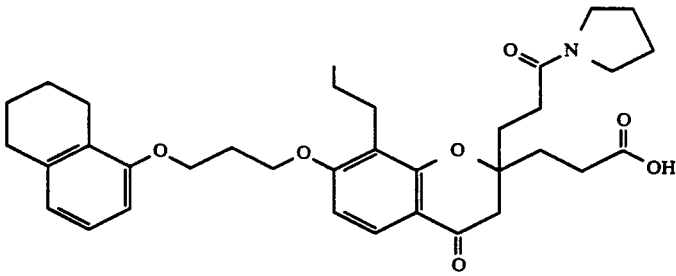

To a solution of 240 mg (0.40 mmol) of the title product of Example 51 in 4 ml of methanol was added 0.15 ml of a 50% aqueous solution of sodium hydroxide and 1 ml of water. The mixture was stirred for 1 hour at reflux and then permitted to cool. The cooled reaction mixture was partitioned between ethyl acetate and 3N hydrochloric acid, and the aqueous layer was further extracted with two portions of ethyl acetate. The combined organic extracts were washed with brine, dried over sodium sulfate, filtered, and the solvent removed under reduced pressure. Chromatography of the residue over silica gel, using methanol/ethyl acetate/acetic acid as eluent, gave a glass which was triturated with diethyl ether to give the title compound (61 mg) as a solid, m.p. 160°-164° C.

Analysis for C₃₅H₄₅NO₇ (MW=591.75):
Calcd.: C, 71.04; H, 7.66; N, 2.37.
Found: C, 70.60; H, 7.65; N, 2.29.

EXAMPLE 53

3,4-dihydro-4-hydroxy-7-(3-phenoxypropoxy)-8-propyl-2H-1-benzopyran-2,2-dipropanoic acid

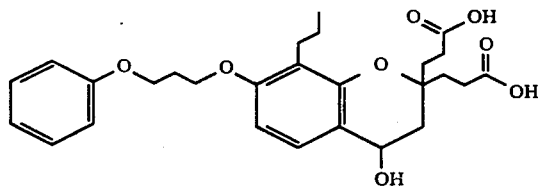

To a stirred solution of 78 mg (2.1 mmol) of NaBH₄ in 2 ml of water at 0° C. is added over 3 minutes a solution of 250 mg (0.515 mmol) of the title product of Example 17 in 3 ml of tetrahydrofuran (THF). After 30 minutes at 0° C., the mixture was permitted to warm to room temperature, and a further 2 ml each of water and of THF were added. After one hour, the reaction mixture was acidified with 3N hydrochloric acid, and the mixture was extracted with three portions of ethyl acetate. The combined organic extracts were washed with brine, dried (Na₂SO₄), the drying agent removed by filtration, and the solvent removed under reduced pressure. Crystallization of the residue from 50% ethyl acetate/hexane gave the title compound (150 mg), m.p. 131.5°–132.5° C.

Analysis for $C_{27}H_{34}O_8$ (MW=486.57):
Calcd.: C, 66.65; H, 7.04.
Found: C, 66.78; H, 6.64.

EXAMPLE 54

3,4-dihydro-4-hydroxy-8-propy-7-[3-[(5,6,7,8-tetrahydro-1-naphthalenyl)oxy]propoxy]-2H-1-benzopyran-2,2-dipropanol

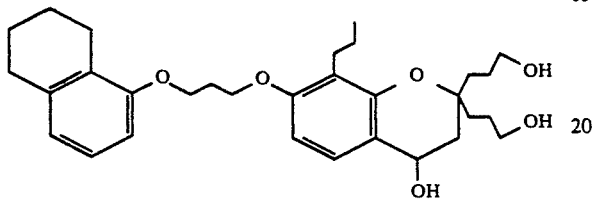

To a stirred suspension of 319 mg (8.40 mmol) of LiAlH₄ in 12 ml of tetrahydrofuran (THF) at 0° C. was added a solution of 1.00 g (1.68 mmol) of the title product of Example 42 in 5 ml of tetrahydrofuran. After one-half hour, the mixture was permitted to warm to room temperature, and stirred further for two hours. The reaction was then quenched by sequentially adding 320 μl of water, 320 μl of 15% aqueous sodium hydroxide, and 960 μl of water. The formed salts were removed by filtration, and the solvent removed under reduced pressure to give the title compound (770 mg) as a white solid, m.p. 123°–123.5° C.

Analysis for $C_{31}H_{44}O_6$ (MW=512.69):
Calcd.: C, 72.62; H, 8.65.
Found: C, 72.59; H, 8.79.

EXAMPLE 55 diethyl 3,4-dihydro-7-(3-phenoxypropoxy)-8-propyl-2H-1-benzopyran-2,2-dipropanoate

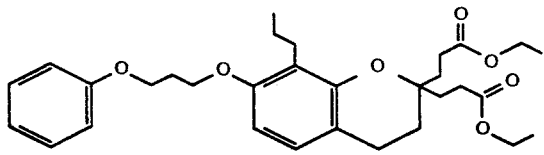

A mixture of 370 mg (0.941 mmol) of the title product of Example 44, 243 mg (1.13 mmol) of 1-bromo-3-phenoxypropane, and 273 mg (1.98 mmol) of anhydrous potassium carbonate in 10 ml of dimethylformamide was stirred overnight at room temperature. Thereafter, the solvent was removed under reduced pressure, and the residue was partitioned between ethyl acetate and water. The aqueous layer was separated, acidified with 3N hydrochloric acid, and the layers reshaken. The aqueous layer was further extracted with two portions of ethyl acetate. The combined organic extracts were dried over magnesium sulfate, and the solvent was removed under reduced pressure. The title compound (185 mg) was obtained after chromatography on silica gel using 20% ethyl acetate/hexane as eluent.

Analysis for $C_{31}H_{42}O_7$ (MW=526.68):
Calcd.: C, 70.69; H, 8.04.
Found: C, 70.67; H, 7.95.

EXAMPLE 56

3,4-dihydro-7-(3-phenoxypropoxy)-8-propyl-2H-1-benzopyran-2,2-dipropanoic acid

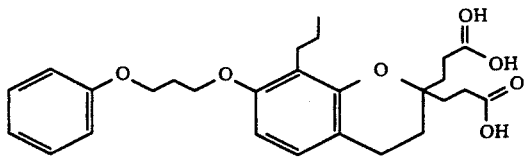

The title compound (118 mg), m.p. 130.5°–132.5° C., was prepared by the method of Example 22 substituting the title product of Example 55 (140 mg) for the title product of Example 21.

Analysis for $C_{27}H_{34}O_7$ (MW=470.57):
Calcd.: C, 68.91; H, 7.28.
Found: C, 68.54; H, 7.15.

EXAMPLE 57

2-bromo-1-tetrahydropyranyloxyethane

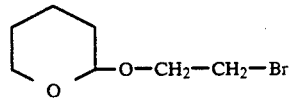

The title compound was prepared according to the method disclosed in *J. Am. Chem. Soc.*, 1948, 70, 4187.

EXAMPLE 58

2-(5,6,7,8-tetrahydro-1-naphthoxy)-1-tetrahydropyranyloxyethane

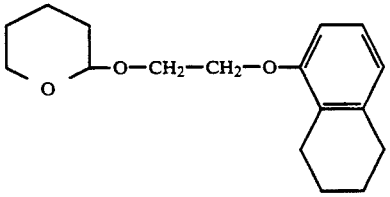

A mixture of 1.48 g (10 mmol) of 5,6,7,8-tetrahydro-1-naphthol, 0.34 g (1.0 mmol) of tetra-n-butylammonium hydrogen sulfate, 6.27 g (30 mmol) of the title product of Example 57, 20 ml of methylene chloride, 9 ml of water, and 11 ml of 1N sodium hydroxide was stirred vigorously overnight at reflux. The organic layer was separated, and the solvent removed under reduced pressure. The residue was triturated with diethyl ether and filtered to remove the insolubles. The ether solution was sequentially washed with two portions of dilute aqueous sodium hydroxide, with water, and then with brine. After drying over magnesium sulfate, the solution was filtered and the solvent was removed under reduced pressure. Chromatography of the residue on silica gel, using 5% ethyl acetate/hexane as eluent gave 730 mg of the title compound.

¹H NMR (CDCl₃): δ7.01(dd, J=7 Hz, J=7 Hz, 1H); 6.66(d, J=7 Hz, 1H); 6.64(d, J=7 Hz, 1H); 4.73(br s, 1H); 4.20–3.38(m, 6H); 2.69(m, 4H); and 1.90–1.45(m, 10H).

EXAMPLE 59

2-(5,6,7,8-tetrahydro-1-naphthoxy)ethanol

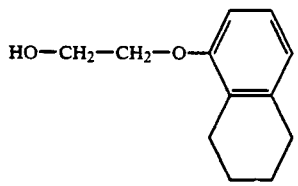

A solution of 700 mg (2.54 mmol) of the title product of Example 58 in a mixture of 9 ml of acetic acid, 3 ml of tetrahydrofuran, and 3 ml of water was stirred at 85°–90° C. After 3.5 hours, 4 drops of concentrated sulfuric acid were added and stirring continued for an additional one-half hour. The mixture was permitted to cool, and 4 g of sodium carbonate monohydrate was added. The resulting mixture was partitioned between diethyl ether and water. The organic layer was washed repeatedly with saturated aqueous sodium bicarbonate, with water, and then with brine. The solution was dried over magnesium sulfate, the drying agent was removed by filtration, and the solvent was removed under reduced pressure. Chromatography of the residue on silica gel, using 15% ethyl acetate/toluene as eluent, gave 216 mg of the title compound.

$^1$H NMR (CDCl$_3$): δ7.11(dd, J=7 Hz, J=7 Hz, 1H); 6.68(d, J=7 Hz, 1H); 6.61(d, J=7 Hz, 1H); 4.04(m, 4H); 2.70(m, 4H); 1.76(m, 4H); and 1.56(s, 1H).

EXAMPLE 60 diethyl 3,4-dihydro-4-oxo-8-propyl-7-[2-[(5,6,7,8-tetrahydro-1-naphthalenyl)oxy]ethoxy]-2H-1-benzopyran-2,2-dipropanoate

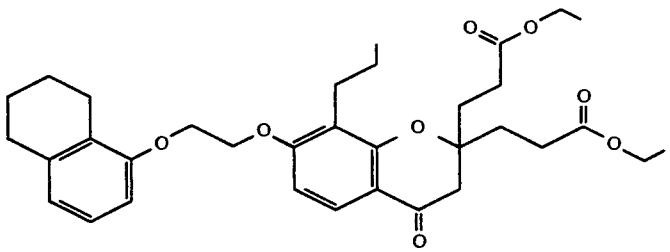

A solution of 202 mg (1.05 mmol) of the title product of Example 59 in 10 ml of CH$_2$Cl$_2$ was cooled with stirring to 0° C. and treated sequentially with 370 mg (3.70 mmol) of triethylamine and 362 mg (3.15 mmol) of methanesulfonyl chloride. After one hour, the mixture was treated with another 370 mg of triethylamine and 362 mg of methanesulfonyl chloride. After one-half hour, the mixture was washed successively with water, aqueous sodium bicarbonate solution, dilute aqueous hydrochloric acid, and water. The organic phase was dried (MgSO$_4$), filtered, and the solvent removed under reduced pressure. The residue was taken up in 10 ml of dimethylformamide. To the resulting solution was added 406 mg (1.00 mmol) of the title product of Example 1 and 290 mg (2.10 mmol) of anhydrous potassium carbonate. The mixture was stirred overnight at room temperature. Another 290 mg of potassium carbonate was then added, and stirring was continued at 60° C. for six hours. The mixture was allowed to cool, and the solvent was removed under reduced pressure. The residue was partitioned between ethyl acetate and water. The aqueous layer was further extracted with two portions of ethyl acetate. The combined organic extracts were washed successively with water and with brine, dried (Na$_2$SO$_4$), filtered, and the solvent removed under reduced pressure. The residue was chromatographed over silica gel. Elution with 15% ethyl acetate/toluene produced 152 mg of the title compound as a solid.

$^1$H NMR (CDCl$_3$): δ7.71(d, 1H); 7.04(d, 1H); 6.73(d, 1H); 6.70 (d, 1H); 6.59(d, 1H); 4.34(m, 4H); 4.10(q, 4H); 2.85–1.43(m, 22H); 1.24 (t, 6H); and 0.90(t, 3H).

EXAMPLE 61

3,4-dihydro-4-oxo-8-propyl-7-[2-[(5,6,7,8-tetrahydro-1-naphthalenyl)oxy]ethoxy]-2H-1-benzopyran-2,2-dipropanoic acid

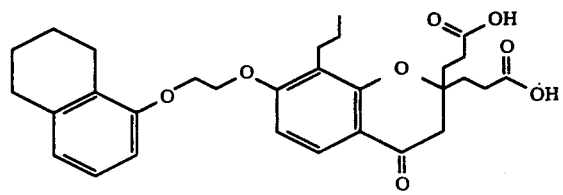

A mixture of 150 mg (0.277 mmol) of the titled product of Example 60, 3 ml of methanol, and 3 ml of 1N sodium hydroxide was stirred at reflux for one hour. The reaction mixture was permitted to cool and then partitioned between ethyl acetate and 3N hydrochloric acid. The aqueous layer was further extracted with two portions of ethyl acetate. The combined organic extracts were washed with brine, dried (MgSO$_4$), filtered, and the solvent removed under reduced pressure. Crystallization of the residue from ethyl acetate gave 24 mg of the title compound as a solid, m.p. 159.5°–161.5° C.

Analysis for C$_{30}$H$_{36}$O$_8$ (MW=524.62):
Calcd.: C, 68.68; H, 6.92.
Found: C, 68.43; H, 6.96.

EXAMPLE 62

N-(2-propylidine)cyclohexylamine

The title compound was prepared by the method disclosed in *J. Org. Chem.*, 19, 1054 (1954).

EXAMPLE 63 nona-1,8-dien-5-one

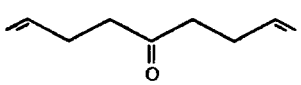

To a solution of 16.0 g (158 mmol) of diisopropylamine in 150 ml of tetrahydrofuran at 0° C. was added 158 ml of a 1.0M solution of n-butyllithium in hexane. The reaction mixture was cooled to −30° C., and to it was added a solution of 20.2 g (144 mmol) of the title product of Example 62 in 75 ml of tetrahydrofuran. After 1.0 hour at −30° C., the mixture was cooled to −70° C. To the resulting mixture was then added 26.1 g of allyl bromide in 38 ml of tetrahydrofuran. After 10 minutes, the mixture was permitted to warm to room temperature, and after 2 hours, it was poured into brine. The aqueous layer was further extracted with diethyl ether. After drying the combined extracts over sodium sulfate followed by filtration, the solvent was removed and the residue distilled to give a crude product (8.53 g) which was used without further purification. A solution of 4.14 g of the crude material in 13 ml of tetrahydrofuran was added to a mixture of 2.57 g of diisopropylamine, 25.4 ml of a 1.0M solution of n-butyllithium in hexane, and 25 ml of tetrahydrofuran at −30° C. The resulting mixture was kept for one hour at −30° C., and thereafter 3.0 g of allyl bromide was added. After stirring overnight at room temperature, the mixture was poured into brine, the aqueous layer extracted with diethyl ether, and the combined organic solutions dried over sodium sulfate. After filtration, the solvent was removed, and the residue was then stirred overnight in a mixture of 50 ml of diethyl ether and 50 ml of 3N hydrochloric acid. The mixture was then poured into brine and the aqueous layer was further extracted with diethyl ether. The combined organic extracts were dried over magnesium sulfate, and filtered. The solvents were removed by distillation through a Vigreaux column at atmospheric pressure. Distillation of the residue at 5 mm of pressure gave the title compound (719 mg), suitable for use in the next reaction step.

$^H$NMR (CDCl$_3$): δ6.05–4.83(m, 6H); and 2.68–2.05(m, 8H).

IR (CHCl$_3$) 1715 cm$^{-1}$, 1642 cm$^{-1}$.

EXAMPLE 64

2,2-bis(but-3-enyl)-2,3-dihydro-8-propyl-7-hydroxy-4H-1-benzopyran-4-one

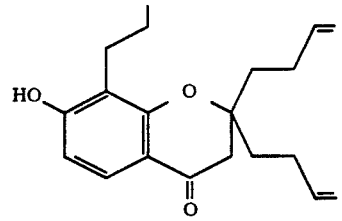

A mixture of 719 mg (5.21 mmol) of the title product of Example 63, 970 mg (5.00 mmol) of 2,4-dihydroxy-3-propylacetophenone, 360 mg (5.00 mmol) of pyrrolidine, and 5.5 ml of toluene containing 2.0 g of 3A molecular sieves was stirred at reflux for six hours, then kept overnight at room temperature, the solution was then decanted from the sieves, and the sieves were washed with methylene chloride. The solvent was then removed under reduced pressure. Chromatography of the residue over silica gel, using 14:5:1 methylene chloride:hexane:ethylacetate as eluent, gave the title compound (439 mg) as a solid.

Analysis for C$_{20}$H$_{20}$O$_3$ (MW=314.43):
Calcd.: C, 76.40; H, 8.34.
Found: C, 76.31; H, 8.47.

EXAMPLE 65

2,2-bis(but-3-enyl)-2,3-dihydro-8-propyl-7-[3-[(5,6,7,8-tetrahydro-1-naphthelenyl)oxy]propoxy]-4H-1-benzopyran-4-one

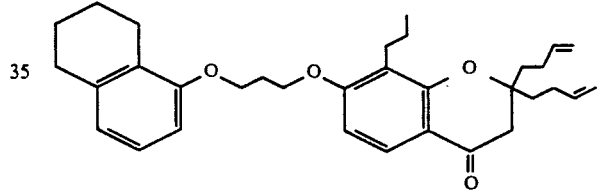

A solution of 366 mg (1.17 mmol) of the title product of Example 64 and 695 mg (2.04 mmol) of the title product of Example 12 in 11 ml of dry dimethylforamide was treated with 338 mg (2.45 mmol) of anhydrous potassium carbonate. The mixture was stirred for 2 hours at 80° C., then permitted to cool. The solvent was removed under reduced pressure, and the residue was partitioned between ethyl acetate and water. The aqueous layer was extracted with a fresh portion of ethyl acetate. The combined organic extracts were washed with brine, dried over magnesium sulfate, filtered, and the solvent evaporated. The residue was chromatographed over silica gel to give 503 mg of the title compound.

$^1$H NMR (CDCl$_3$): δ7.70(d, 1H); 7.01(dd, 1H); 6.64(d, 1H); 6.58(d, 1H); 6.54(d, 1H); 6.01–4.81(m, 6H); 4.20(t, 2H); 4.13(t, 2H); 2.80–1.23 (m, 24H); and 0.90(t, 3H).

EXAMPLE 66

2,2-bis(3,4-dihydroxybutyl)-2,3-dihydro-8-propyl-7-[3-[(5,6,7,8-tetrahydro-1-naphthalenyl)oxy]propoxy]-4H-1-benzopyran-4-one

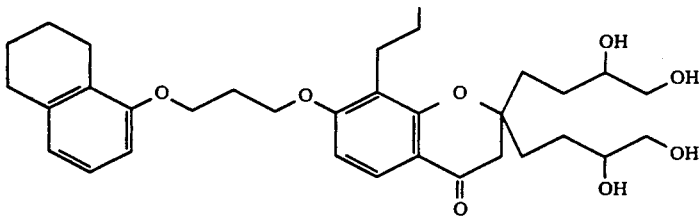

To a solution of 500 mg (1.00 mmol) of the title product of Example 58 in a mixture of 4.8 ml of t-butanol and 1.5 ml of tetrahydrofuran (THF) was added successively 0.5 ml of water, 288 mg (2.13 mmol) of N-methylmorpholine-N-oxide, and 0.2 ml of a 1% solution of osmium tetraoxide ($OsO_4$) in t-butanol. After 2.5 hours, the reaction mixture was directly applied to a column of silica gel. Elution of the column with 15% methanol/methylene chloride gave a crude product which was triturated with diethyl ether to give the title compound (453 mg) as a hemihydrate, m.p.=113°–115° C.

Analysis for $C_{33}H_{46}O_8 \cdot \frac{1}{2}H_2O$ (MW=594.74):
Calcd.: C, 68.38; H, 8.17.
Found: C, 68.02; H, 7.93.

EXAMPLE 67

3,4-dihydro-4-oxo-8-propyl-7-[3-[(5,6,7,8-tetrahydro-1-naphthalenyl)oxy]propoxy]-2H-1-benzopyran-2,2-dipropanal

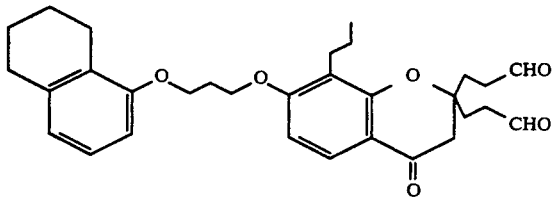

To a solution of 90 mg (0.158 mmol) of the title product of Example 66 in 3.7 ml of t-butanol was added a solution of 135 mg (0.629 mmol) of sodium periodate in 1.0 ml of $H_2O$. After stirring at room temperature for 2 hours, the mixture was partitioned between diethyl ether and water and the aqueous layer extracted with a fresh portion of ether. The combined organic extracts were washed with brine, dried over magnesium sulfate, filtered, and the solvent removed under reduced pressure. The residue was triturated with diethyl ether to give the title compound (61 mg), m.p. 107°–108° C.

Analysis for $C_{31}H_{38}O_6$ (MW=506.65):
Calcd.: C, 73.48; H, 7.56.
Found: C, 73.09; H, 7.76.

EXAMPLE 68 undeca-1,10-dien-6-one

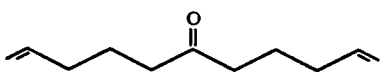

To a solution of 10.7 g of diisopropylamine in 100 ml of tetrahydrofuran at 0° C. was added 74.1 ml of a 1.43M solution of n-butyllithium in hexane. After 15 minutes the solution was cooled to −30° C. To the mixture was then added a solution of 13.5 g of the title product of Example 62 in 50 ml of tetrahydrofuran, and the resulting mixture was kept for 1 hour at −30° C. The mixture was then cooled to −65° C. and to it was added a solution of 19.6 g of 4-bromo-1-butene in 25 ml of tetrahydrofuran. The mixture was then permitted to warm to room temperature overnight. The mixture was poured into brine, and the aqueous layer was extracted with two portions of diethyl ether. The combined organic extracts were dried over sodium sulfate, filtered, and the solvent removed under reduced pressure. Distillation of the residue gave 10.68 g of material which was dissolved in 30 ml of tetrahydrofuran, then added to a cooled mixture (−30° C.) of 8.5 ml of diisopropylamine 42.7 ml of a 1.43M solution of n-butyllithium in hexane, and 50 ml of tetrahydrofuran. After 1 hour, the mixture was cooled to −65° C., and a solution of 11.2 g of 4-bromo-1-butene in 15 ml of tetrahydrofuran. After permitting the mixture to warm to room temperature overnight, the mixture was poured into brine, and the aqueous layer extracted with two portions of diethyl ether. The combined organic extracts were dried over magnesium sulfate, filtered, and the solvent removed in vacuo. The residue (13.8 g) was then stirred overnight in a mixture of 100 ml of diethyl ether and 100 ml of dilute hydrochloric acid. The layers were separated, and the aqueous layer was extracted with two portions of diethyl ether. The combined organic extracts were washed with brine, dried over magnesium sulfate, and filtered. The solvent was removed by distillation through a Vigreaux column at atmospheric pressure. Continued distillation gave the title compound (4.39 g), b.p. 85°–87° C. at 2.0 mm.

Analysis for $C_{11}H_{18}O$ (MW=166.27):
Calcd.: C, 79.43; H, 10.91.
Found: C, 79.54; H, 11.01.

EXAMPLE 69

2,3-dihydro-2,2-bis(pent-4-enyl)-8-propyl-7-hydroxy-4H-1-benzopyran-4-one

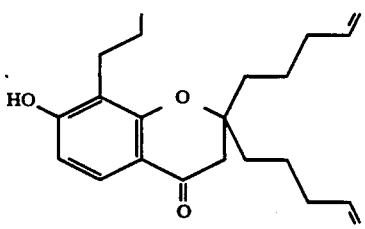

A mixture of 3.93 g (20.2 mmol) of 2,4-dihydroxy-3-propylacetophenone, 3.36 g (20.2 mmol) of the title product of Example 68, 1.44 g (20.2 mmol) of pyrrolidine, and 23.5 ml of toluene was stirred at reflux under a water separator containing 3A molecular sieves for 5 hours. The mixture was then permitted to cool, and the solvent was removed under reduced pressure. Chromatography of the residue over silica gel using 25% ethyl acetate/hexane as eluant gave the title compound (5.85 g) as a dark red oil.

¹H NMR (CDCl³): δ8.33(br s, 1H); 7.62(d, 1H); 6.53(d, 1H); 6.02–4.73(m, 6H); 2.82–1.17(m, 18H); and 0.97(t, 3H).

¹H NMR (CDCl₃): δ7.68(d, 1H); 7.00(dd, 1H); 6.68(d, 1H); 6.65(d, 1H); 6.53(d, 1H); 6.00–4.76(m, 6H); 4.21(t, 2H); 4.13(t, 2H); 2.83–1.23(m, 28H); and 0.93(t, 3H).

EXAMPLE 71

2,3-dihydro-2,2-bis(4,5-dihydroxypentyl)-8-propyl-7-[3-[(5,6,7,8-tetrahydro-1-naphthalenyl)oxy]propoxy]-4H-1-benzopyran-4-one

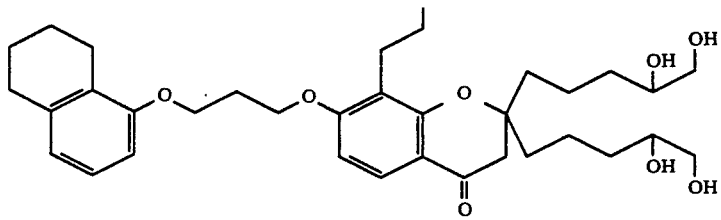

EXAMPLE 70

2,3-dihydro-2,2-bis(pent-4-enyl)-8-propyl-7-[3-[(5,6,7,8-tetrahydro-1-naphthalenyl)oxy]propoxy]-4H-1-benzopyran-4-one

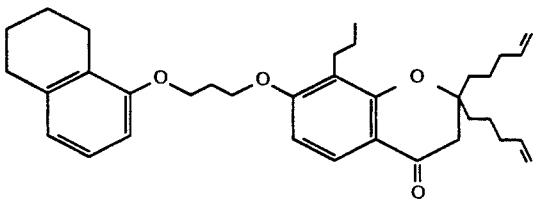

To a solution of 3.0 g (9.55 mmol) of the title product of Example 69 and 4.01 g (11 mmol) of the title product of Example 12 in 56 ml of dry dimethylformamide (DMF) was added 2.77 g (20.1 mmol) of anhydrous potassium carbonate. The resulting mixture was stirred overnight at room temperature. The solvent was removed in vacuo, and the residue was partitioned between ethyl acetate and 3N hydrochloric acid. The aqueous layer was further extracted with two portions of ethyl acetate. The combined organic extracts were washed with water and with brine, dried over magnesium sulfate, filtered, and the solvent removed under reduced pressure. Chromatography of the residue over silica gel, using 10% ethyl acetate/hexane as eluent, gave the title compound (4.19 g) as an oil.

To a solution of 1.00 g (1.99 mmol) of the title product of Example 70 in a mixture of 9.5 ml of t-butanol, 2.9 ml of tetrahydrofuran, and 0.95 ml of water was added 576 mg (4.26 mmol) of N-methylmorpholine-N-oxide followed by 0.4 ml of a 1% solution of osmium tetraoxide (OsO₄) in t-butanol. After 2.5 hours at room temperature, the reaction mixture was directly applied to a column of silica gel. Elution with 15% methanol/methylene chloride gave a glass which was triturated with diethyl ether to give the title compound (830 mg), m.p. 87°–88° C.

Analysis for C₃₅H₅₀O₈ (MW=598.78):
Calcd.: C, 70.21; H, 8.42.
Found: C, 69.95; H, 8.41.

EXAMPLE 72

3,4-dihydro-4-oxo-8-propyl-7-[3-[(5,6,7,8-tetrahydro-1-naphthalenyl)oxy]propoxy]-2H-1-benzopyran-2,2-dibutanal

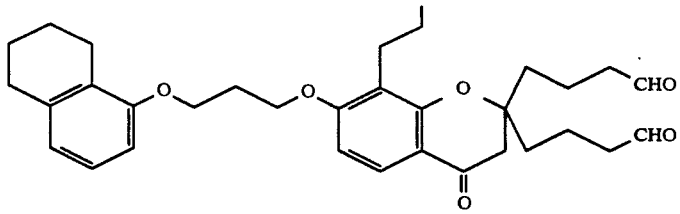

To a solution of 200 mg (0.350 mmol) of the title product of Example 71 in 9.8 ml of t-butanol was added with stirring a solution of 300 mg (1.40 mmol) of sodium periodate in 2.2 ml of water. After two hours, the mixture was partitioned between diethyl ether and water. The organic layer was washed with brine, dried over sodium sulfate, filtered, and the solvent removed under reduced pressure. The residue was chromatographed on a silica gel column, using ethyl acetate/hexane as eluent. Crystallization from diethyl ether/hexane gave 114 mg of the title compound, m.p. 72°–73° C.

Analysis for C₃₃H₄₂O₆ (MW=534.70):
Calcd.: C, 74.14; H, 7.92.
Found: C, 74.25; H, 7.94.

EXAMPLE 73

3,4-dihydro-4-oxo-8-propyl-7-[3-[(5,6,7,8-tetrahydro-1-naphthalenyl)oxy]propoxy]-2H-1-benzopyran-2,2-dibutanoic acid -continued

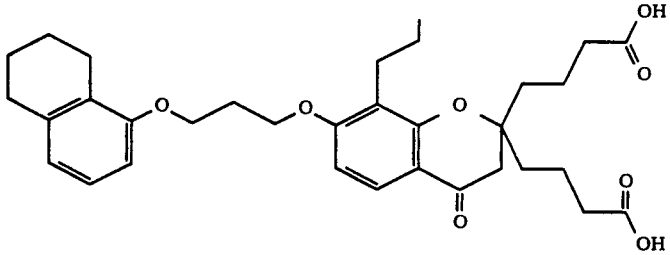

To a solution of 98 mg (0.183 mmol) of the title product of Example 72 in 3.1 ml of dioxane was added a solution of 87 mg (0.89 mmol) of sulfamic acid in 0.8 ml of water. The solution was cooled in an ice bath, and a solution of 84 mg of 80% sodium chlorate in 0.8 ml of water was added. After one hour, diethyl ether was added, and the organic layer was washed five times with water, once with brine. The solution was dried over magnesium sulfate, filtered, and the solvent removed in vacuo to give the title compound (92 mg), m.p. 138°–138.5° C.

Analysis for $C_{33}H_{42}O_8$ (MW=566.70):
Calcd.: C, 69.95; H, 7.47.
Found: C, 69.93; H, 7.55.

EXAMPLE 74

2,2-bis[4,5-bis(acetyloxy)pentyl]-2,3-dihydro-8-propyl-7-[3-[(5,6,7,8-tetrahydro-1-naphthalenyl)oxy]propoxy]-4H-1-benzopyran-4-one

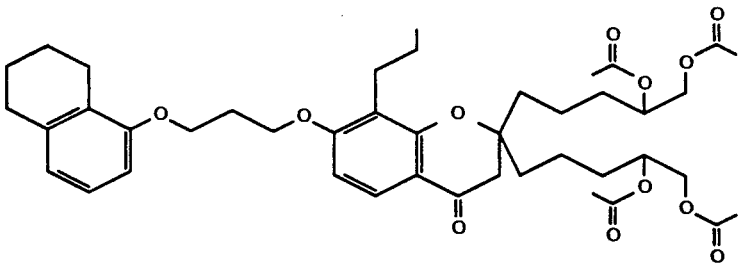

To a solution of 404 mg (0.708 mmol) of the title product of Example 71 in 4.4 ml of pyridine was added 0.70 ml (7.4 mmol) of acetic anhydride. After stirring overnight at room temperature, the mixture was taken up in ethyl acetate, and washed sequentially with two portions of aqueous sodium bicarbonate, water, and brine. The organic layer was dried over magnesium sulfate, filtered, and the solvent removed under reduced pressure. Chromatography of the residue over silica gel, using 40% ethyl acetate/hexane as the eluent, gave the title compound (314 mg).

Analysis for $C_{43}H_{58}O_{12}$ (MW=766.93):
Calcd.: C, 63.35; H, 7.62.
Found: C, 67.23; H, 7.67.

EXAMPLE 75 diethyl 3,4-dihydro-7-(octyloxy)-4-oxo-8-propyl-2H-1-benzopyran-2,2-dipropanoate

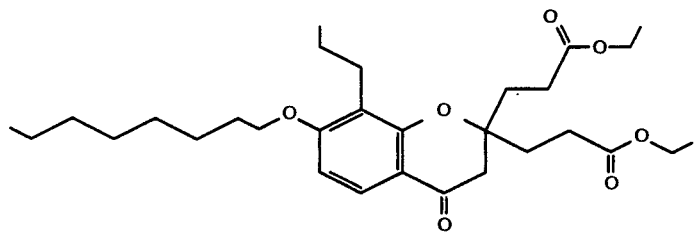

The title compound (381 mg) was prepared by the method of Example 18 substituting the title product of Example 1 (406 mg; 1.00 mmol) for the title product of Example 2, and further substituting 1-bromooctane (232 mg; 1.20 mmol) for benzyl bromide.

$^1$H NMR (CDCl$_3$): δ7.69(d, 1H); 6.53(d, 1H); 4.10(q, 4H); 3.99 (t, 2H); 2.64(br s, 2H); 1.24(t, 6H); 0.95(t, 3H); and 0.90(t, 3H).

EXAMPLE 76

3,4-dihydro-7-(octyloxy)-4-oxo-8-propyl-2H-1-benzopyran-2,2-dipropanoic acid

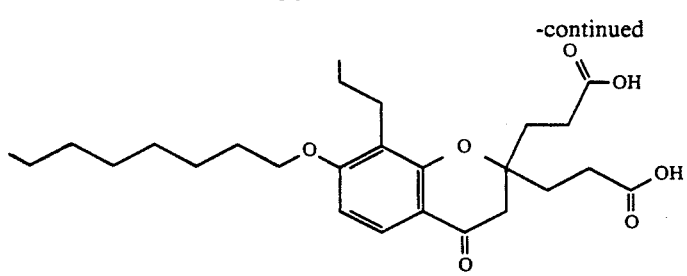

The title compound (231 mg), m.p. 147.5°–148.5° C., was prepared by the method of Example 20 substituting the title product of Example 75 (361 mg) for the title product of Example 19 and carrying out the reaction for 1.5 hours at reflux instead of for 2 hours at room temperature.

Analysis for $C_{26}H_{38}O_7$ (MW=462.59):
Calcd.: C, 67.51; H, 8.28.
Found: C, 67.69; H, 8.48.

EXAMPLE 77 diethyl 7-(decyloxy)-3,4-dihydro-4-oxo-8-propyl-2H-1-benzopyran-2,2-dipropanoate

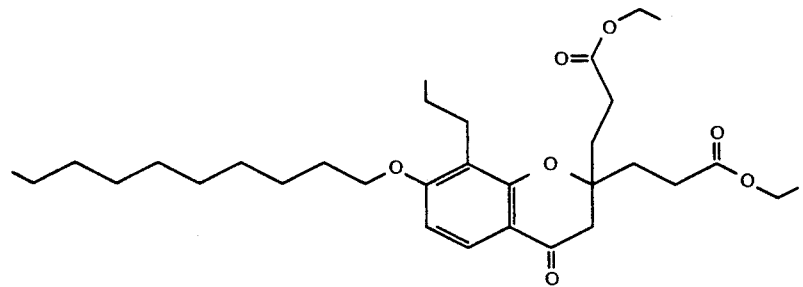

To a mixture of 406 mg (1.00 mmol) of the title product of Example 1, 190 mg (1.20 mmol) of 1-decanol, and 393 mg (1.50 mmol) of triphenylphosphine in 10 ml of dimethylformamide was added 261 mg (1.50 mmol) of diethyl azodicarboxylate. After stirring overnight at room temperature, the solvent was removed under reduced pressure. Chromatography of the residue on silica gel, using 20% ethyl acetate/hexane as eluent, gave 408 mg of the title compound.

$^1$H NMR (CDCl$_3$): δ7.70(d, 1H); 6.51(d, 1H); 4.09(q, 4H); 3.99(t, 2H); 2.63(br s, 2H); 1.23(t, 6H); 0.94(t, 3H); and 0.88(t, 3H).

EXAMPLE 78

7-(decyloxy)-3,4-dihydro-4-oxo-8-propyl-2H-1-benzopyran-2,2-dipropanoic acid

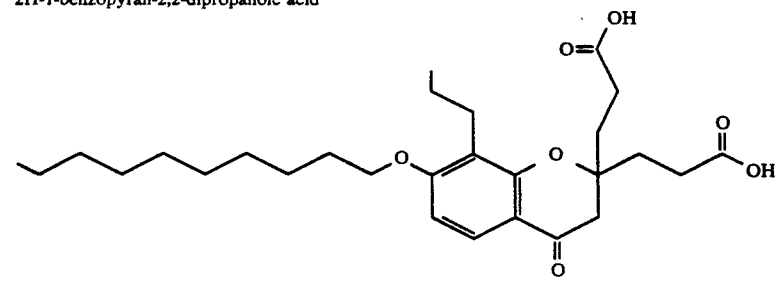

The title compound (198 mg), m.p. 144°–146° C., was prepared by the method of Example 20 substituting the title product of Example 77 for the title product of Example 19, and carrying out the reaction for two hours at reflux instead of for two hours at room temperature.

Analysis for $C_{28}H_{42}O_7$ (MW=490.64):
Calcd.: C, 68.55; H, 8.63.
Found: C, 68.47; H, 8.66.

EXAMPLE 79 diethyl 7-(hexyloxy)-3,4-dihydro-4-oxo-8-propyl-2H-1-benzopyran-2,2-dipropanoate

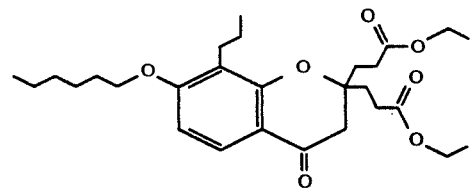

The title compound (388 mg) was prepared by the method of Example 18 substituting the title product of Example 1 (406 mg; 1.00 mmol) for the title product of Example 2, and further substituting 1-bromohexane (198 mg, 1.20 mmol for benzyl bromide.

1H NMR (CDCl3): δ7.69(d, 1H); 6.51(d, 1H); 4.11(q, 4H); 3.99 (t, 2H); 2.64(br s, 2H); 1.25(t, 6H); 0.95(t, 3H); and 0.91(t, 3H).

EXAMPLE 80

7-(hexyloxy)-3,4-dihydro-4-oxo-8-propyl-2H-1-benzopyran-2,2-dipropanoic acid

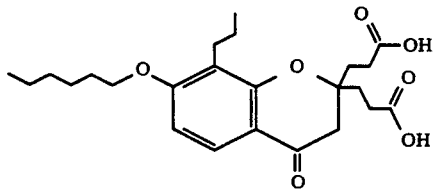

The title compound (168 mg) was prepared by the method of Example 20 substituting the title product of Example 79 for the title product of Example 19, and carrying out the reaction for 1 hour at reflux instead of for 2 hours at room temperature. The product was crystallized from ethyl acetate, m.p. 164.5°–165° C.

Analysis for C24H34O7 (MW=434.54):
Calcd.: C, 66.35; H, 7.89.
Found: C, 66.10; H, 7.97.

EXAMPLE 81 diethyl 6-acetyl-3,4-dihydro-8-propyl-7-hydroxy 2H-1-benzopyran-2,2-dipropanoate

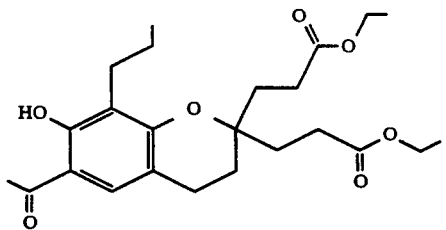

To a solution of 790 mg (2.01 mmol) of the title product of Example 44 in 4 ml of acetic acid was added 547 mg (4.02 mmol) of anhydrous zinc chloride. The mixture was stirred for six hours at reflux, and then permitted to cool. The mixture was partitioned between ethyl acetate and dilute hydrochloric acid. The aqueous layer was further extracted with two portions of ethyl acetate. The combined organic extracts were washed successively with five portions of aqueous sodium bicarbonate, water, and then brine. The extracts were dried over sodium sulfate, filtered, and the solvent removed under reduced pressure. Chromatography of the residue over silica gel using 25% ethyl acetate-hexane as eluent gave the title compound, 230 mg.

1H NMR (CDCl3): δ12.55(s, 1H); 7.29(s, 1H); 4.13(q, 4H); 2.54(s, 3H); 2.90–1.43(m, 14H); 1.25(t, 6H); 0.95(t, 3H).

EXAMPLE 82 diethyl 6-acetyl-3,4-dihydro-8-propyl-7-[3-[(5,6,7,8-tetrahydro-1-naphthalenyl)oxy]propoxy]-2H-1-benzopyran-2,2-dipropanoate

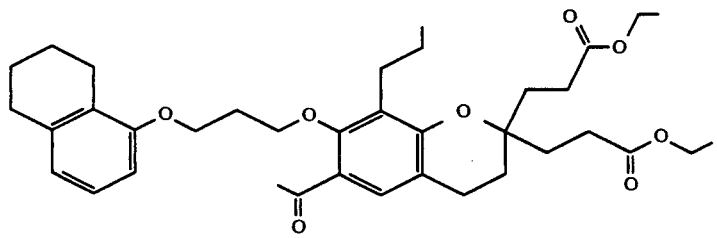

A mixture of 204 mg (0.469 mmol) of the title product of Example 81, 378 mg (1.41 mmol) of the title product of Example 12, and 136 mg (0.985 mmol) of anhydrous potassium carbonate in 4 ml of dimethylformamide was stirred at 80° for six hours. A further 136 mg of potassium carbonate was added, and the mixture was heated for another six hours. The mixture was permitted to cool and was partitioned between ethyl acetate and dilute hydrochloric acid. The aqueous layer was further extracted with two portions of ethyl acetate. The combined organic extracts were washed with brine, dried over sodium sulfite, filtered, and the solvent removed under reduced pressure. Chromatography of the residue over silica gel using 15% ethyl acetate/toluene as eluent gave the title compound, 114 mg.

Analysis for C37H50O8 (MW=622.81):
Calcd.: C, 71.36; H, 8.09.
Found: C, 71.48; H, 8.08.

EXAMPLE 83

6-acetyl-3,4-dihydro-8-propyl-7-[3-[(5,6,7,8-tetrahydro-1-naphthalenyl)oxy]propoxy]-2H-1-benzopyran-2,2-dipropanoic acid

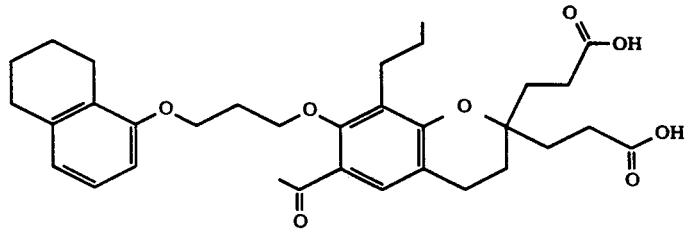

A mixture of 50 mg (0.080 mmol) of the title product of Example 77, 3 ml of methanol, and 1 ml of 1N aqueous sodium hydroxide was stirred at reflux for one hour. The mixture was allowed to cool, and was partitioned between ethyl acetate and dilute hydrochloric acid. The aqueous layer was further extracted with two portions of ethyl acetate. The combined organic extracts were washed with brine, dried over magnesium sulfate, filtered, and the solvent removed under reduced pressure to give the title compound (35 mg), as an oil.

Analysis for $C_{33}H_{42}O_8$ (MW=566.70):
Calcd.: C, 69.69; H, 7.47.
Found: C, 70.28; H, 7.86.

EXAMPLE 84

3,4-dihydro-4-oxo-7-(3-phenoxypropoxy)-8-propyl-2H-1-benzopyran-2,2-dipropanoic acid, dipotassium salt

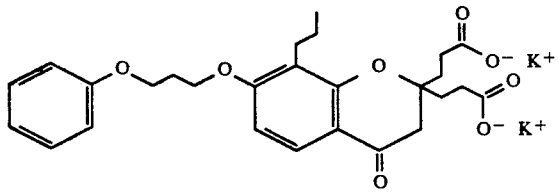

To a suspension of 250 mg (0.515 mmol) of the title product of Example 17 in 5 ml of water was added a solution of 71 mg (0.52 mmol) of anhydrous potassium carbonate in 5 ml of water. A 5 ml portion of methanol was added, and the resulting mixture was warmed to effect solution. The solvent was evaporated under a stream of nitrogen, and the residue was dried by azeotropic distillation with toluene to give the title compound, 269 mg, isolated as the hemihydrate.

Analysis for $C_{27}H_{30}K_2O_8 \cdot \frac{1}{2}H_2O$ (MW=569.75):
Calcd.: C, 56.91; H, 5.48.
Found: C, 56.55; H, 5.71.

What is claimed is:

1. A compound of the formula:

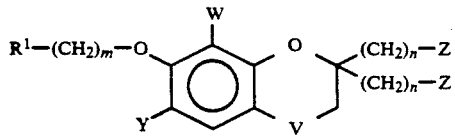

or a pharmaceutically acceptable addition salt thereof, wherein $R^1$ is methyl, phenyl,

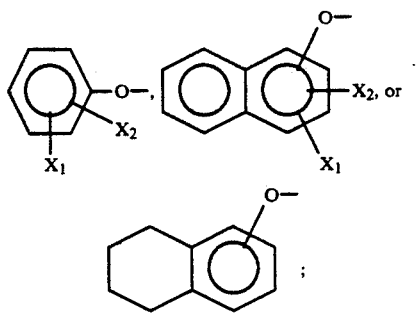

wherein $X_1$ and $X_2$ may be the same or different and are members of the group consisting of hydrogen, —Cl, —Br, —CF$_3$, —NH$_2$, —NO$_2$, or straight or branched chain alkyl of 1-3 carbon atoms;

wherein m is an integer from 1-9;
wherein n is an integer from 1-5;
wherein V is —CH(OH—, or —CH$_2$—;
wherein W is hydrogen or straight or branched chain alkyl of 1-6 carbon atoms;
wherein Y is hydrogen or —COCH$_3$ with the proviso that when W is hydrogen Y is not hydrogen;
wherein both Z moieties are —CHO, —COOR$^2$, —COR$^3$,

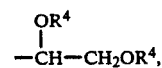

or CH$_2$OR$^4$ with the exception that when one Z moiety of Formula I is COOR$^2$, the other Z moiety may be COR$^3$;

wherein R$^2$ is hydrogen, a pharmaceutically acceptable cation, straight or branched chain alkyl having 1-6 carbon atoms,

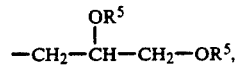

CH(CH$_2$OR$^5$)$_2$ with the proviso that when Z is —COOR$^2$, the R$^2$ substituent in one —COOR$^2$ moiety may be the same or different form the R$^2$ substituent in the other COOR$^2$ moiety;

wherein R$^3$ is

and wherein R$^7$ and R$^8$ may be the same or different and are members of the group comprising hydrogen or straight or branched chain alkyl having 1-6 carbon atoms;

wherein R$^4$ is hydrogen, or

wherein R$^5$ is hydrogen, benzyl-, or straight or branched chain alkyl of 1-3 carbon atoms; and
wherein R$^6$ is straight or branched chain alkyl of 1-6 carbon atoms.

2. A compound according to claim 1 of the formula:

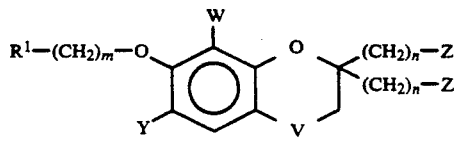

or a pharmaceutically acceptable salt thereof, wherein R$^1$ is methyl, phenyl,

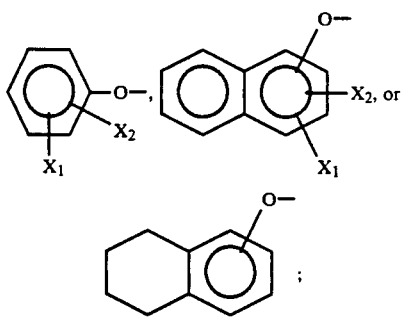

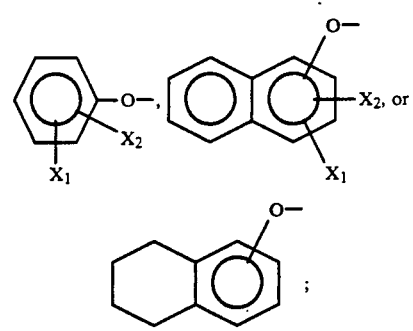

wherein X₁ and X₂ may be the same or different and are hydrogen, —Cl, —Br, —CF₃, —NH₂, and —NO₂, or straight or branched chain alkyl of 1-3 carbon atoms;

wherein m is an integer from 1-9;
wherein n is an integer from 1-5;
wherein V is —CH(OH)—, or —CH₂—;
wherein W is hydrogen or straight or branched chain alkyl of 1-6 carbon atoms;
wherein Y is hydrogen or —COCH₃;
wherein both Z moieties are —CHO, —COOR², —COR³, with the exception that when one Z moiety of Formula I is —COOR², the other Z moiety may be —COR³;
wherein R² is hydrogen, a pharmaceutically acceptable cation, straight or branched chain alkyl having 1-6 carbon atoms,

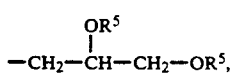

or —CH(CH₂OR⁵)₂ with the proviso that when Z is —COOR², the R² substituent in one —COOR² moiety may be the same or different from the R² substituent in the other—COOR² moiety;
wherein R³ is

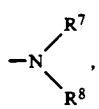

and wherein R⁷ and R⁸ may
be the same or different and are members of the group comprising hydrogen or straight or branched chain alkyl having 1-6 carbon atoms; and
wherein R⁵ is hydrogen, benzyl, or straight or branched chain alkyl having 1-3 carbon atoms.

3. A compound according to claim 1 of the formula:

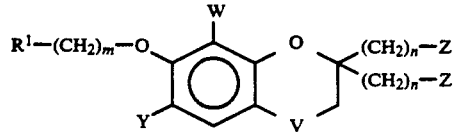

or a pharmaceutically acceptable salt thereof, wherein R¹ is methyl, phenyl, wherein X₁ and Xₓ may be the same or different and are hydrogen, —Cl, —Br, —CF₃, —NH₂, —NO₂, or lower alkyl of 1-3 carbon atoms;

wherein m is an integer from 1-9;
wherein n is an integer from 1-5;
wherein V is —CH(OH)—, or —CH₂—;
wherein W is hydrogen or straight or branched chain alkyl of 1-6 carbon atoms;
wherein Y is hydrogen or COCH₃;
wherein Z is —CH₂OR⁴, or

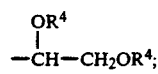

wherein R⁴ is a member of the group comprising hydrogen or

and
wherein R⁶ is straight or branched chain alkyl of 1-6 carbon atoms.

4. A compound according to claim 1 wherein R¹ is

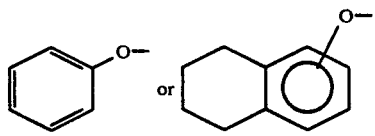

5. A compound according to claim 2 of the formula:

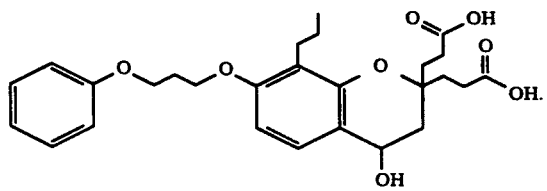

6. A compound according to claim 2 of the formula:

7. A compound according to claim 2 of the formula:

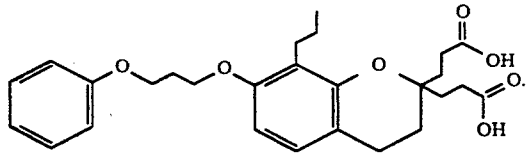

8. A compound according to claim 2 of the formula:

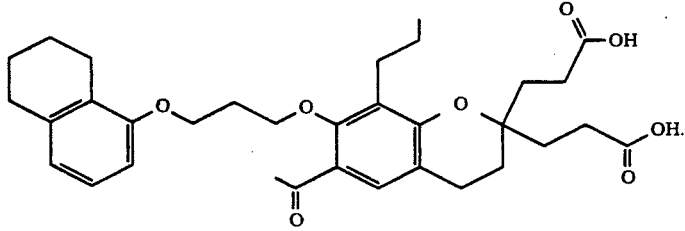

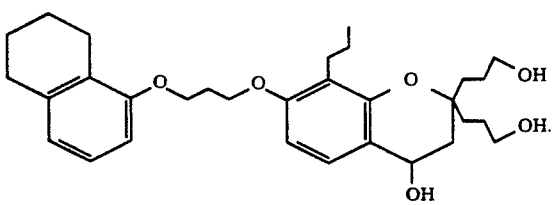

9. A pharmaceutical composition for treating allergies or inflammation comprising a therapeutically effective amount of a compound according to claim 1 in a pharmaceutically acceptable carrier.

10. A pharmaceutical composition according to claim 9 for treating allergies or inflammation comprising a therapeutically effective amount of a compound of the formula

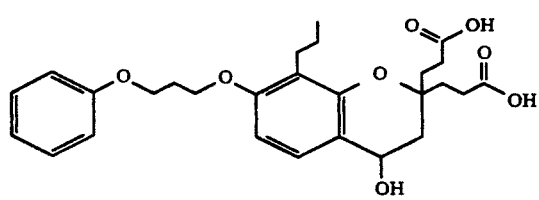

in a pharmaceutically acceptable carrier.

11. A pharmaceutical composition according to claim 9 for treating allergies or inflammation comprising a therapeutically effective amount of a compound of the formula in a pharmaceutically acceptable carrier.

12. A pharmaceutical composition according to claim 9 for treating allergies or inflammation comprising a therapeutically effective amount of a compound of the formula

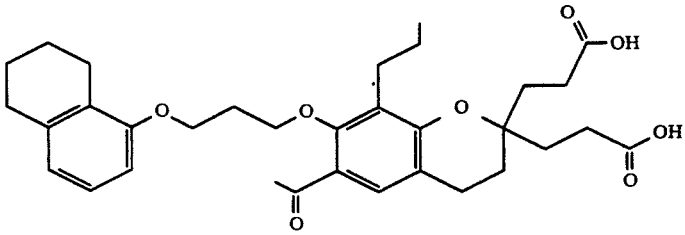

in a pharmaceutically acceptable carrier.

13. A pharmaceutical composition according to claim 9 for treating allergies or inflammation comprising a therapeutically effective amount of a compound of the formula

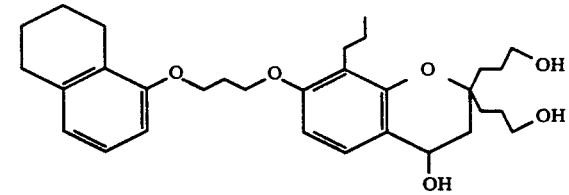

in a pharmaceutically acceptable carrier.

14. A method of treating $LTD_4$ mediated allergic reactions or inflammatory conditions in mammals comprising administering a therapeutically effective amount of a pharmaceutical composition according to claim 9 to a mammal in need of such treatment.

15. A method of treating $LTD_4$ mediated allergic reactions or inflammatory conditions in mammals comprising administering a therapeutically effective amount of the pharmaceutical composition of claim 10 to a mammal in need of such treatment.

16. A method of treating $LTD_4$ mediated allergic reactions or inflammatory conditions in mammals comprising administering a therapeutically effective among of the pharmaceutical composition of claim 11 to a mammal in need of such treatment.

17. A method of treating LTD$_4$ mediated allergic reactions or inflammatory conditions in mammals comprising administering a therapeutically effective amount of the pharmaceutical composition of claim 12 to a mammal in need of such treatment.

18. A method of treating LTD$_4$ mediated allergic reactions or inflammatory conditions in mammals comprising administering a therapeutically effective amount of the pharmaceutical composition of claim 13 to a mammal in need of such treatment.

* * * * *